US011633481B2

(12) United States Patent
Asirvatham

(10) Patent No.: US 11,633,481 B2
(45) Date of Patent: **\*Apr. 25, 2023**

(54) SURFACTANTS FOR USE IN HEALTHCARE PRODUCTS

(71) Applicant: AdvanSix Resins & Chemicals LLC, Parsippany, NJ (US)

(72) Inventor: Edward Asirvatham, Chatham, NJ (US)

(73) Assignee: AdvanSix Resins & Chemicals LLC, Parsippany, NJ (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/120,040

(22) Filed: Dec. 11, 2020

(65) Prior Publication Data

US 2021/0187110 A1 Jun. 24, 2021

Related U.S. Application Data

(60) Provisional application No. 62/951,943, filed on Dec. 20, 2019.

(51) Int. Cl.

| | | |
|---|---|---|
| *A61K 47/24* | (2006.01) | |
| *A61K 9/00* | (2006.01) | |
| *A61K 9/06* | (2006.01) | |
| *A61K 9/107* | (2006.01) | |
| *A61K 9/16* | (2006.01) | |
| *A61K 31/5377* | (2006.01) | |
| *A61K 31/55* | (2006.01) | |
| *A61K 47/10* | (2017.01) | |
| *A61K 47/26* | (2006.01) | |
| *A61K 47/44* | (2017.01) | |
| *C07F 7/08* | (2006.01) | |

(52) U.S. Cl.
CPC ............ *A61K 47/24* (2013.01); *A61K 9/0019* (2013.01); *A61K 9/0056* (2013.01); *A61K 9/06* (2013.01); *A61K 9/107* (2013.01); *A61K 9/1611* (2013.01); *A61K 9/1617* (2013.01); *A61K 9/1623* (2013.01); *A61K 9/1635* (2013.01); *A61K 9/1652* (2013.01); *A61K 31/5377* (2013.01); *A61K 31/55* (2013.01); *A61K 47/10* (2013.01); *A61K 47/26* (2013.01); *A61K 47/44* (2013.01); *C07F 7/0838* (2013.01)

(58) Field of Classification Search
CPC ............ C07F 7/02; C07F 7/08; C07F 7/0834; C07F 7/0838; A61K 9/00; A61K 9/0019; A61K 9/0056; A61K 9/06; A61K 9/107; A61K 9/1611; A61K 9/1617; A61K 9/1623; A61K 9/1635; A61K 9/1652
See application file for complete search history.

(56) References Cited

U.S. PATENT DOCUMENTS

| | | |
|---|---|---|
| 3,624,120 A | 11/1971 | Yetter |
| 3,929,678 A | 12/1975 | Laughlin et al. |
| 5,041,590 A | 8/1991 | Snow |
| 5,162,155 A | 11/1992 | Berndt et al. |
| 6,013,683 A | 1/2000 | Hill et al. |
| 7,622,512 B2 | 11/2009 | Schorzman et al. |
| 10,053,619 B2 | 8/2018 | Saboowala et al. |
| 11,008,348 B2 | 5/2021 | Asirvatham et al. |
| 2007/0099805 A1 | 5/2007 | Phenis et al. |
| 2007/0104778 A1 | 5/2007 | Zeng et al. |
| 2007/0142583 A1 | 6/2007 | Schorzman et al. |
| 2008/0152540 A1* | 6/2008 | Schorzman ........... B65B 25/008 422/40 |
| 2010/0063310 A1 | 3/2010 | Knepper et al. |
| 2010/0215959 A1 | 8/2010 | Jonschker et al. |
| 2012/0093746 A1 | 4/2012 | Moriya |
| 2013/0130508 A1 | 5/2013 | Wu et al. |
| 2018/0057732 A1 | 3/2018 | Babcock et al. |
| 2018/0177774 A1* | 6/2018 | Kandavilli ............. A61Q 19/08 |
| 2018/0193231 A1* | 7/2018 | Jung ..................... A61K 8/0225 |

(Continued)

FOREIGN PATENT DOCUMENTS

| | | |
|---|---|---|
| CN | 102614808 A | 8/2012 |
| CN | 104826140 A | 8/2015 |

(Continued)

OTHER PUBLICATIONS

Fluhr JW, Gloor M, Lehmann L, Lazzerini S, Distante F, Berardesca E. Glycerol accelerates recovery of barrier function in vivo. Acta Derm Venereol. Nov. 1999;79(6):418-21. (Year: 1999).*
Grgic, J., Pedisic, Z., Saunders, B. et al. International Society of Sports Nutrition position stand: sodium bicarbonate and exercise performance. J Int Soc Sports Nutr 18, 61 (2021). (Year: 2021).*
Mero, A.A., Hirvonen, P., Saarela, J. et al. Effect of sodium bicarbonate and beta-alanine supplementation on maximal sprint swimming. J Int Soc Sports Nutr 10, 52 (2013). (Year: 2013).*

(Continued)

*Primary Examiner* — Brandon J Fetterolf
*Assistant Examiner* — Manahil Mirghani Ali Abdalhameed
(74) *Attorney, Agent, or Firm* — Faegre Drinker Biddle & Reath LLP

(57) ABSTRACT

Healthcare formulations, including, inventive surfactants, Active ingredient formulated as solids, liquids, or emulsions. The present disclosure provides formulations of healthcare products, such as: prescription drugs, over the counter drugs; minerals, herbal, and/or vitamin supplements; drugs administered in hospitals, clinics, physician's office, and places of palliative care; vaccines, tissue, organ, and cell transplants and/or grafts and/or infusions; and wound care formulations including topical ointments, lotions, cleaners, wipes, bandages, and dressings. The Active may be included in the formulations as a solute, a solvent, a particle, or an oil immiscible component of the formulation. The Active may be included in tablets, capsules, tinctures, liquids, or emulsions. Inventive healthcare formulations include formulations suitable for administration orally, topically, and/or by injection.

13 Claims, 7 Drawing Sheets

(56) References Cited

U.S. PATENT DOCUMENTS

| | | |
|---|---|---|
| 2018/0362716 A1 | 12/2018 | Okamura |
| 2019/0112549 A1 | 4/2019 | Bauer et al. |
| 2020/0148831 A1 | 5/2020 | Okamura |
| 2020/0231608 A1 | 7/2020 | Okamura |
| 2021/0054002 A1 | 2/2021 | Asirvatham et al. |
| 2021/0186842 A1 | 6/2021 | Asirvatham |
| 2021/0187460 A1 | 6/2021 | Asirvatham |
| 2021/0188882 A1 | 6/2021 | Asirvatham |
| 2021/0189292 A1 | 6/2021 | Asirvatham |
| 2021/0198555 A1 | 7/2021 | Asirvatham |
| 2021/0230194 A1 | 7/2021 | Asirvatham et al. |
| 2021/0238479 A1 | 8/2021 | Asirvatham |

FOREIGN PATENT DOCUMENTS

| | | |
|---|---|---|
| CN | 107497365 A | 12/2017 |
| CN | 107522726 A | 12/2017 |
| CN | 107602862 A | 1/2018 |
| CN | 107698615 A | 2/2018 |
| EP | 0164514 A1 | 12/1985 |
| EP | 0436359 A2 | 7/1991 |
| EP | 2024423 A2 | 2/2009 |
| EP | 2458622 A2 | 5/2012 |
| GB | 1429143 A | 3/1976 |
| GB | 1470250 A | 4/1977 |
| GB | 1473201 A | 5/1977 |
| GB | 1473202 A | 5/1977 |
| KR | 10-2015-0108143 A | 9/2015 |
| TW | 201307372 A | 2/2013 |
| WO | 00/26206 A1 | 5/2000 |
| WO | 02/46517 A1 | 6/2002 |
| WO | 2007/075320 A2 | 7/2007 |
| WO | 2007/141565 A2 | 12/2007 |
| WO | 2009/085297 A2 | 7/2009 |
| WO | 2015/041214 A1 | 3/2015 |
| WO | 2016/191148 A1 | 12/2016 |
| WO | 2021/003455 A1 | 1/2021 |
| WO | 2021/034550 A1 | 2/2021 |

OTHER PUBLICATIONS

M. Isabel Carretero, Manuel Pozo, Clay and non-clay minerals in the pharmaceutical and cosmetic industries Part II. Active ingredients, Applied Clay Science, vol. 47, Issues 3-4, 2010, pp. 171-181, ISSN 0169-1317. (Year: 2010).*

Atalay PB, Kuku G, Tuna BG. Effects of carbendazim and astaxanthin co-treatment on the proliferation of MCF-7 breast cancer cells. In Vitro Cell Dev Biol Anim. Feb. 2019;55(2):113-119. (Year: 2018).*

International Search Report and Written Opinion received for PCT Patent Application No. PCT/US20/64345, dated Apr. 12, 2021, 9 pages.

International Search Report and Written Opinion received for PCT Patent Application No. PCT/US20/64347, dated Mar. 10, 2021, 7 pages.

International Search Report and Written Opinion received for PCT Patent Application No. PCT/US20/64684, dated Mar. 25, 2021, 14 pages.

International Search Report and Written Opinion received for PCT Patent Application No. PCT/US20/64687, dated Mar. 31, 2021, 12 pages.

International Search Report and Written Opinion received for PCT Patent Application No. PCT/US20/64692, dated Apr. 7, 2021, 9 pages.

International Search Report and Written Opinion received for PCT Patent Application No. PCT/US20/66027, dated Apr. 7, 2021, 12 pages.

International Search Report and Written Opinion received for PCT Patent Application No. PCT/US20/66031, dated Apr. 8, 2021, 12 pages.

International Search Report and Written Opinion received for PCT Patent Application No. PCT/US2020/045797, dated Oct. 26, 2020, 11 pages.

Stanbro et al., "Cationic silicones for use in contact lens application", Polymer Preprints, 51(2), 2010, pp. 305-306.

* cited by examiner

SURFACTANTS FOR USE IN HEALTHCARE PRODUCTS

CROSS-REFERENCE TO RELATED APPLICATION

This application claims priority to U.S. Provisional Application No. 62/951,943, filed Dec. 20, 2019, the disclosure of which is herein incorporated by reference in its entirety.

FIELD

The present disclosure pertains to surfactants for use in healthcare products. Such surfactants may include siloxane derivatives of amino acids wherein the siloxane derivatives have surface-active properties.

BACKGROUND

Surfactants (molecules with surface-active properties) are widely used in commercial applications in formulations ranging from detergents to hair care products to cosmetics. Compounds with surface-active properties are often added to formulations intended to improve human or animal health. Some healthcare products include pharmaceuticals, nutraceuticals, vitamin and/or mineral supplements, and wound dressings. Surfactant are an important component in many healthcare directed or related formulations, at least in part, because some surfactants help to increase the amount of the Active ingredient, stabilizer, filler, excipient, adjuvant, or the like that can be included in a conveniently sized dose and/or because the inclusion of a surfactant in the formulation is useful in the manufacture and/or packaging of the product.

Surfactants may be uncharged, zwitterionic, cationic, or anionic. Although in principle any surfactant class (e.g., cationic, anionic, nonionic, amphoteric) is suitable in cleansing or cleaning applications, in practice many personal care cleansers and household cleaning products are formulated with a combination of two or more surfactants from two or more surfactant classes.

Often, surfactants are amphiphilic molecules with a relatively water-insoluble hydrophobic "tail" group and a relatively water-soluble hydrophilic "head" group. These compounds may adsorb at an interface, such as an interface between two liquids, a liquid and a gas, or a liquid and a solid. In systems comprising relatively polar and relatively non-polar components the hydrophobic tail preferentially interacts with the relatively non-polar component(s) while the hydrophilic head preferentially interacts with the relatively polar component(s). In the case of an interface between water and oil, the hydrophilic head group preferentially extends into the water, while the hydrophobic tail preferentially extends into the oil. When added to a water-gas interface, the hydrophilic head group preferentially extends into the water, while the hydrophobic tail preferentially extends into the gas. The presence of the surfactant disrupts at least some of the intermolecular interaction between the water molecules, replacing at least some of the interactions between water molecules with generally weaker interactions between at least some of the water molecules and the surfactant. This results in lowered surface tension and can also serve to stabilize the interface.

At sufficiently high concentrations, surfactants may form aggregates which serve to limit the exposure of the hydrophobic tail to the polar solvent. One such aggregate is a micelle. In a typical micelle the molecules are arranged in a sphere with the hydrophobic tails of the surfactant(s) preferentially located inside the sphere and the hydrophilic heads of the surfactant(s) preferentially located on the outside of the micelle where the heads preferentially interact with the more polar solvent. The effect that a given compound has on surface tension and the concentration at which it forms micelles may serve as defining characteristics for a surfactant.

SUMMARY

The present disclosure provides healthcare products formulated with surfactants, such healthcare products include, but are not limited to, tablets, powders, liquids, salves, ointments, cleansers and or wipes for use on the body, and wound dressings. These products may be formulated to include one or more surfactants from one or more surfactant classes disclosed herein.

The present disclosure provides surfactants for use in healthcare products in the form of siloxane derivatives of amino acids that have surface-active properties. The amino acids may be naturally occurring or synthetic amino acids, or they may be obtained via ring-opening reactions of molecules such as lactams, for instance caprolactam. The amino acids may be functionalized with different types of siloxane groups to form compounds with surface-active properties. Characteristically, these compounds may have low critical micelle concentrations (CMC) and/or the ability to reduce the surface tension of a liquid.

The present disclosure provides formulations for delivering an Active to a patient, comprising at least one surfactant of Formula I,

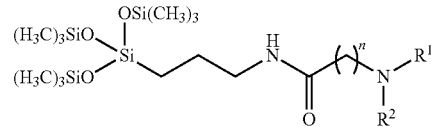

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; and at least one Active ingredient.

The present disclosure further provides a formulation for delivery of an Active to a patient, comprising at least one surfactant of Formula I,

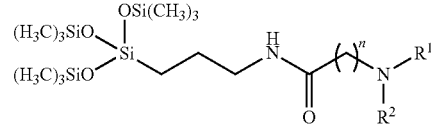

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; and at least one Active ingredient is selected from the group consisting of: at least one drug selected from the groups consisting of, but not limited to: an analgesic, an antibiotic, an anti-hypertensive, a chemotherapeutic, an anti-psychotics, an anti-depressive, a tranquilizer, a proton pump inhibitor, and an anti-fungal.

The present disclosure further provides a formulation in the form of a solid for delivering an Active to a patient, comprising at least one surfactant of Formula I,

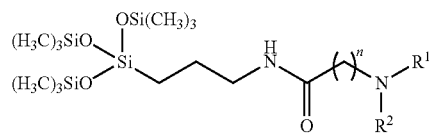

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one Active ingredient, and at least one: excipient selected from the group consisting of: a binder; a disintegrant, a glidant, a colorant, and/or a flavorant.

The present disclosure also provides a formulation for delivering an Active in the form of a liquid, comprising at least one surfactant of Formula I,

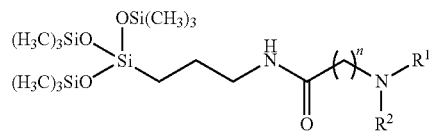

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one Active ingredient; and either or both an aqueous phase and a non-aqueous phase; and optionally at least one colorant, and/or at least one flavorant.

The present disclosure further provides a formulation for delivering an Active in the form of an emulsion, comprising at least one surfactant of Formula I,

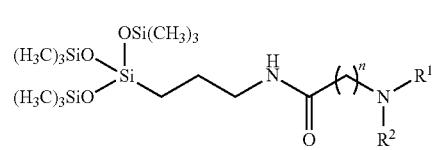

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one Active ingredient an aqueous phase; a non-aqueous; and optionally at least one colorant, and/or at least one flavorant.

The present disclosure further provides a formulation for delivering an Active in the form of an emulsion, comprising at least one surfactant of Formula I,

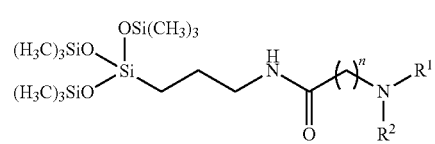

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide;

at least one Active ingredient; an aqueous phase and a non-aqueous; and optionally at least one colorant, and/or at least one flavorant.

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
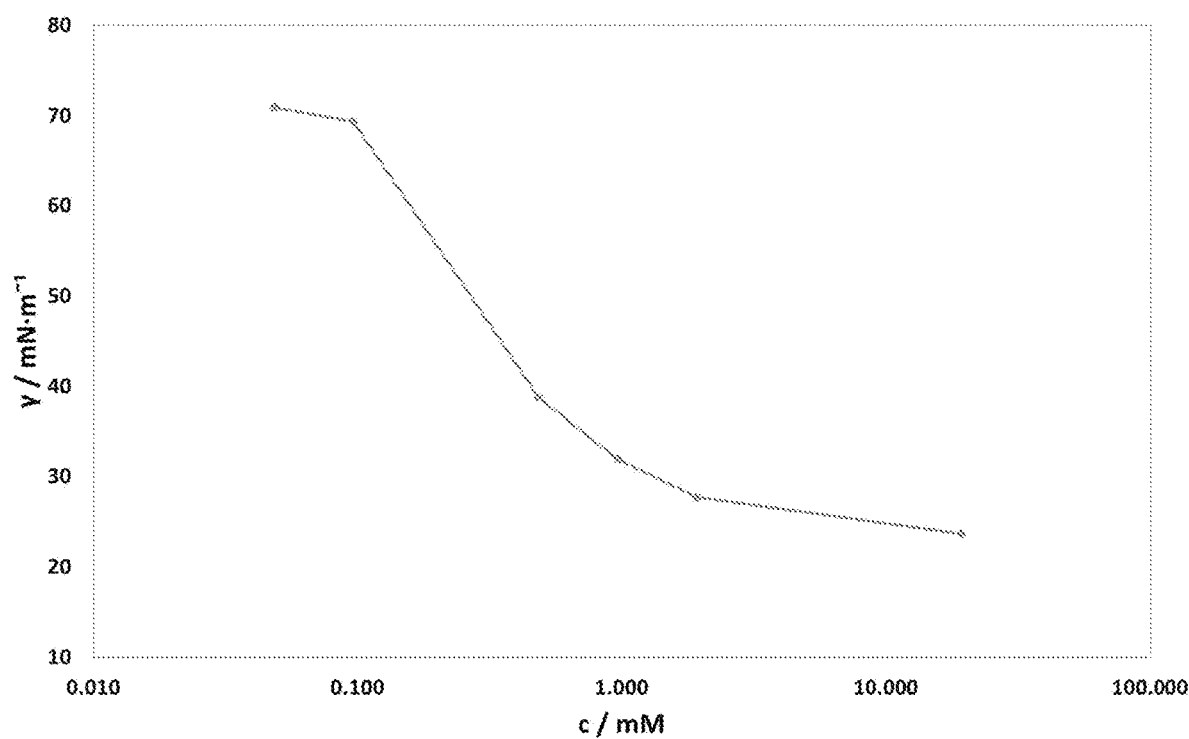
FIG. 1 shows a plot of surface tension versus concentration for Surfactant 2, with a chloride counterion measured at pH=7 as described in Example 1b.

As used herein, the phrase "within any range using these endpoints" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the word "alkyl" means any saturated carbon chain, which may be a straight or branched chain.

As used herein, the phrase "surface-active" means that the associated compound is able to lower the surface tension of the medium in which it is at least partially dissolved, and/or the interfacial tension with other phases, and, accordingly, may be at least partially adsorbed at the liquid/vapor and/or other interfaces. The term "surfactant" may be applied to such a compound.

With respect to the terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm. As used herein, the term "about" means ±5%, ±10%, or ±20% of the value being modified.

The terms "emulsion" or "emulsion formulation" means a colloidal dispersion of two immiscible liquids in the form of droplets, whose diameter, in general, is between 10 nanometers and 100 microns. An emulsion is denoted by the symbol O/W (oil-in-water) if the continuous phase is an aqueous solution and by W/O (water-in-oil) if the continuous phase is an oil. Other examples of emulsions such as O/W/O (oil-in-water-oil) include oil droplets contained within aqueous droplets dispersed in a continuous oil phase. "Physically stable" emulsions will meet the criteria under USP <729>, which defines universal limits for (1) mean droplet size not exceeding 500 nm or 0.5 µm and (2) the population of large-diameter fat globules, expressed as the volume-weighted percentage of fat greater than 5 µm (PFAT5) not exceeding 0.05%, at 5° C. or room temperature for a designated storage time period. In addition, physically stable emulsions will have no visible crystals of Actives upon storage at 5° C. or room temperature for a designated time period. Crystals are considered visible when viewed at magnification of 4× to 10×. An emulsion is physically stable if it meets the criteria under USP <729> and crystals of Actives are not visible upon storage at 5° C. or room temperature for a time period equal to or at least 1 week, 2 weeks, 4 weeks, 1 month, 2 months, 6 months, 1 year or 2 years.

"Chemically stable" emulsions of the disclosure are ones in which the concentration of the Active component (i.e., the therapeutically Active being delivered) does not change by more than about 20% under appropriate storage conditions for at least 1 month. In certain embodiments, the Active's concentration in an emulsion of the present disclosure does not change by more than about 5%, 10%, 15% or 20% under appropriate storage conditions for at least 1, 2, 3, 4, 5, 6, 9, 12, 15, 18, or 24 months. storage conditions for at least 1, 2, 3, 4, 5, 6, 9, 12, 15, 18, or 24 months.

In one example, the stable emulsion compositions of the disclosure are stable over a wide range of temperatures, e.g., −20° C. to 40° C. The compositions of the disclosure may be stored at about 5° C. to about 25° C.

"Oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase. The oil phase refers to the non-aqueous portion of a water-in-oil emulsion.

"Aqueous phase" or "water phase" in a water-in-oil emulsion refers to the water present and any components 45 that are water soluble, i.e., have not exceeded their solubility limit in water. "Aqueous phase", as used herein, includes a water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials. The aqueous phase refers to the non-oil portion of a water-in-oil emulsion.

An "emulsifier" refers to a compound that deters the separation of the injectable emulsion into individual oil and aqueous phases. Emulsifiers useful in the present disclosure generally are (1) compatible with the other ingredients of the stable emulsions of the present disclosure, (2) do not interfere with the stability or efficacy of the drugs contained in the emulsions, (3) are stable and do not deteriorate in the preparation, and (4) are non-toxic.

As used herein the terms "Active or Actives" or "Active ingredient" or "Active ingredients" refer to compounds that act or are thought to act in beneficial manner in a human and/or on an animal, as used here in these terms may be used interchangeably. Such compounds include, but are not limited to, pharmaceuticals, antibodies, graft materials, transplant materials, nutraceutical, vitamins, and mineral supplement, such Actives may be formulated either alone or in combination with other Actives.

As used herein, "native particles" refers to particles of a compound without any other added components, i.e. native particles of Actives are particles containing the Active, wherein the particles do not contain any added excipient(s). "Drug-containing particles" refers to preformed particles comprising "native particles of Active" and one or more excipients. The drug-including particles are necessarily larger in size than the native particles. The drug including particles can be granules, beads, pellets, or other engineered particles or agglomerates that otherwise incorporate the smaller, primary drug particles themselves and can withstand conventional powder handling for flow and transfer.

As used herein and unless otherwise specified, "particle size" and "actual particle size" refer to the particle size of a compound without any other component(s) in the formulation, i.e. the particle size of the native particles of an Active or the particle size of a particle that includes an Active, some of these may be referred to as "drug-in particles".

I. Solid Dosage Formulations that Include at Least One Active

Solid dosage formulations include but are not limited to, at least one Active formulated as a: powder: a tablet, formed either by printing a matrix or by compressing solids, in the presence or absence of at least one liquid; or as a capsule.

Some embodiments include tablets or capsules wherein an Active or an Active particle is formulated in the presence of at least one other non-Active selected from the groups consisting of surfactants, dispersants, excipients, binder, sweeteners, and flavorants.

Some embodiments include tablets wherein an Active or an Active particle is formulated by compressing at least one Active with at least one non-Active selected from the groups consisting of surfactants, dispersants, excipients, binder, sweeteners, and flavorants.

Some embodiments include capsules wherein the Active of Active particle is formulated by capturing at least one active within the same casing as at least one non-Active selected from the groups consisting of surfactants, dispersants, excipients, binder, sweeteners, and flavorants.

Some aspects of the invention are formulations that include high concentrations of at least one Active compound, some of these formulations may exhibit low friability and sufficient hardness to withstand storage and handling while at the same time exhibiting an extremely rapid disintegration rate and when administered orally a generally acceptable taste.

In some aspect, rapidly dispersible solid dosage forms may comprise a porous three dimensionally printed matrix comprising drug-containing particles of Actives and bulk material comprising specific excipients such as at least one disintegrant, and at least one binder and at least one surfactant. The bulk material may further comprise at least one additional excipient such as a glidant, sweetener and/or flavorant.

In some embodiments the matrix may be formed by deposition of a printing fluid to a powder, whereby the particles of the powder become bound by binder. The matrix may be porous with a defined overall bulk density, disintegration (dispersion) time in aqueous fluid, dissolution time in aqueous fluid, and moisture content. Some matrices provide a balance of sufficient hardness, low friability, and a rapid dispersion rate when contacted with or immersed in a small volume of aqueous liquid. Some embodiments of the invention include those wherein: a) the hardness of the matrix ranges from about 1 to about 7 kiloponds (kp), about 1 to about 3 kp; b) the matrix disperses in 10 sec or less when placed in 15 ml of water or in saliva; c) binder is introduced into the matrix by way of printing fluid used to form the matrix; d) binder is introduced into the matrix by way of bulk powder used to form the matrix; e) the matrix comprises about 150 mg to about 600 mg of the Active: f) the matrix comprises 10 to 40 printed incremental layers; g) the thickness (height) of an incremental layer ranges from 0.006 to 0.014 inches or 0.008 to 0.012 inches; h) the matrix is porous and non-compressed.

In some embodiments, the Active is present in crystalline form. All polymorphs thereof are contemplated. The crystallinity of the Active or any other material can be determined by differential scanning calorimetry (DSC) to determine the presence of amorphous material. In some embodiments, the Active is present in amorphous form in the bulk powder or in the matrix.

Some embodiments proved a orodispersible dosage form comprising a three-dimensionally printed matrix comprising bound sweetener, binder, disintegrant, surfactant, and drug containing particles of Active, wherein the binder binds the matrix. The matrix may or may not be bound by the Active itself. If the formulation is formed by way of a printing fluid, ideally the printing fluid does not dissolve any substantial amount of the Active during the three-dimensional printing process.

In some embodiments the Active-containing particles comprise at least one Active, and at least one, at least two, at least three, at least four, or at least five pharmaceutical excipients. In some embodiments, the drug containing particles comprise an Active, at least one binder, at least one surfactant, and at least one disintegrant. The Active containing particles may further comprise sweetener and/or flavorant. In some embodiments, the drug-containing particles comprise OXC, at least two binders, at least one surfactant, and at least one disintegrant. Some embodiments of the invention include those wherein: a) content of drug-containing particles in the matrix generally ranges from 55-85% wt, 60-80% wt or 65-70% wt. based upon the total weight of matrix in the final dosage form; b) the drug-containing particles comprise disintegrant, binder, surfactant and native particles of the Active c) the content of native particles of OXC in the drug-containing particles ranges from 55-85% wt., 60-80% wt. or 65-70% wt., based upon the final weight of the drug-containing particles; d) the content of disintegrant in the drug-containing particles ranges from 0-30 wt. %, 1-15 wt. %, or 2-5 wt. %, based upon the final weight of the drug-containing particles; e) the content of binder in the drug-containing particles ranges from 0-10 wt. %, 1-7 wt. %, or 2-5 wt. %, based upon the final weight of the drug-containing particles: f) the content of surfactant in the drug-containing particles ranges from 0-10 wt. %, 1-5 wt. %, or 1.4-4.2 wt. %, based upon the final weight of the drug-containing particles; g) the drug containing particles are manufactured by wet granulation.

One aspect of the invention provides an orodispersible three-dimensionally printed matrix comprising: at least one Active, at least one sweetener, at least one binder, at least one disintegrant, at least one surfactant, and at least one glidant; wherein the matrix comprises particles bound by binder, the matrix is porous and non-compressed; the matrix disperses in less than 15 sec in a volume of 15 ml of aqueous fluid; the Active is included in drug-containing particles comprising small particles of the Active and at least one pharmaceutical excipient as carrier, and the content of the Active in the matrix ranges from 35-60% wt. based upon the total weight of the matrix.

Drug-including particles, especially granules prepared by wet granulation, can be used to prepare rapidly dispersible 3DP matrices comprising Actives having a hardness in the range of 1-3 kP and a dispersion time in water of 15 sec or less, or 10 Sec or less. Suitable drug-containing particles comprise 65-70 wt. % Active, 21.5-23 wt. % diluent/disintegrant, e.g. microcrystalline cellulose, 3-5 wt. % super-disintegrant, e.g. ecoscarmellose, 1-4.5 wt. % surfactant, e.g. sodium lauryl sulfate, and 2.5-5 wt. % binder, e.g. hydroxypropylcellulose. Drug containing particles produced by high shear wet granulation had a DVO.5 of about 60-100 microns.

In some embodiments the matrix rapidly disperses (disintegrates) in a small amount of aqueous fluid. Some embodiments of the invention include those wherein the matrix disperses in about 30 sec or less, about 20 sec or less, about 15 sec or less, about 10 sec or less, or about 5 Sec or less when placed in a small amount of aqueous fluid. In some embodiments, the disintegration time is determined according to USP <701>.

1. Actives

Active may include any compound that has or is thought to have a beneficial effect on human or animal health. Such Actives include, but are not limited to, pharmaceutical compounds which may be available exclusively by prescription or without a prescription; supplements such as vitamins, minerals; baby formula; and meal replacement, energy drinks and/or bars, and the like.

The Active-including particles have an average, mean or median particle size in the range of about 50 to about 400 microns, about 50 to about 300 microns, about 50 to about 250 microns, about 60 to about 250 microns, about 60 to about 100 microns, or about 75 to about 250 microns.

In some embodiments, Active native particles have an average, mean or median particle size in the range of about 1 to about 90 microns, about 1 to about 75 microns, about 1 to about 50 microns, about 1 to about 30 microns, about 1 to about 15 microns, about 1 to about 10 microns, about 2 to about 14 microns, about 10 to about 80 microns, about 20 to about 70 microns, about 20 to about 60 microns or about 30 to about 50 microns. In some embodiments, OXC natives particles have a particle size distribution with a DV90 of less than about 100 microns, a DV90 of less than about 90 microns, a DV90 of less than about 75 microns, a DV90 of less than about 50 microns, and/or have a DV50 of less than about 75 microns, a DV50 of less than about 50 microns, a DV50 of less than about 40 microns, a DV50 of less than about 30 microns, a DV50 of less than about 20 microns, a DV50 of less than about 10 microns, a DV50 of less than about 5 microns, a DV50 of about 1 to about 40 microns, a DV50 of about 1 to about 30 microns, a DV50 of about 1 to about 20 microns, a DV50 of about 5 to about 15 microns and/or have a DV10 of less than about 30 microns, a DV10 of less than about 20 microns, a Dv10 of less than about 10 microns, a Dv10 of less than about 5 microns, a DV10 of less than about 1 microns. All combinations of these DV10, DV50 and DV90 values and ranges are contemplated. The native particle size distribution and/or effective particle size distribution can be mono-modal, bi modal or multi-modal. The Active can be present as a mixture of two or more different native drug powders each having its own native particle size distribution and/or method of preparation. The drug-containing particles can be present as a mixture of two or more different powders each having its own effective particle size distribution and/or method of preparation. In some embodiments, the Active comprises a milled first form and a micronized second form. The amount of first form can range from 0-25% wt., 10-15% wt. or 13-15% wt., and the amount of second form can range 100-75% wt., 90-85% wt., or 97-85% wt., respectively.

Some embodiments of the invention include those wherein the Active including matrix comprises about 150 to about 1200 mg, about 150 mg, about 300 mg, about 450 mg, about 600 mg, about 750 mg, about 900 mg, about 1050 mg or about 1200 of the Active.

2. Excipients

Excipients, in healthcare formulations, are commonly defined inactive compounds added to solid formulations to serve as mediums, and/or fillers in the formulation. Most pharmaceutically acceptable excipients, both small molecules and polymers, can be employed, which allow a pharmaceutically Active ingredient to be loosely encased in a porous structure (a matrix of bound particles) that is subject to rapid dispersion in the presence of an appropriate aqueous fluid, e.g., saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

Unless explicitly stated otherwise as used herein excipients may refer to compounds used as, or commonly referred to as, fillers, diluents, bulking agents and the like, it being understood that these designations are not exhaustive and that they are not exclusive, for example, a specific excipient may serve at both a diluent and a filler. Unless explicitly stated otherwise as used herein, excipients may refer to compounds used as, or commonly referred to as, binders, coatings, disintegrants, sweeteners, flavorants, and gliders.

Excipients may affect the stability, organoleptic properties, and/or physical properties of a given formulation. The weight ratio of Actives to excipients in a given formulation of an Active can be varied to change the therapeutic, physical, appearance, and or organoleptic properties of a given formulation.

Suitable types of excipients for a solid dosage forms include; binders, disintegrants, dispersants, fillers, sweeteners, glidants, flavorants, surfactants, humectants, preservatives and diluents. Although conventional pharmaceutical excipients may be used, they may not always function in precisely the same manner as with traditional pharmaceutical processing.

The addition of at least one excipient in a formulation of an Active may have an impact upon properties of the formulation such as the hardness, dispersion time, friability, dosage form size and dose of drug in the dosage form. If the excipient content in the drug-containing particles is too low, performance of the dosage may be sacrificed. If excipient content in the drug-containing particles is too high, the dosage form size may have to be increased in order to include a suitable dose of the Active therein.

3. Binders

Binders are a sub-class of excipients which may be added to solid formulation. Solid formulations of Active often a binder a compound that promotes association between particles in the solid formulations such as the same or other Actives and or other components including other excipient such as, sweeteners, falovorants, and preservatives, Suitable binders that may be used in the inventive formulations, include, but are not limited to, gelatin, cellulose, derivative of cellulose, polyvinylpryrrolidones, starches, and sugars. Exemplary binders include but are not limited to: spray dried lactose, fructose. sucrose, dextrose, sorbitol, mannitol, xylitol.

One or more binders can be included in the printed matrix. The binder may be included in either the bulk powder, drug containing particles and/or in the printing fluid dispensed through the printhead. The binder is independently selected upon each occurrence. Adhesion of the particles to and/or by the binder occurs either when the binder is contacted by the printing fluid from the printhead or when it is present (i.e., soluble) in the printing fluid. The binder is preferably water soluble, aqueous fluid soluble, partially water soluble or partially aqueous fluid soluble. In some embodiments, the printing fluid comprises 0-10% wt. of binder. In some embodiments, the bulk powder comprises >0 to 50% wt., 10% to 45%, 20% to 45%, 25-40%, 25-35% wt. of binder. In some embodiments, the drug-containing particles comprise >0 to 10%, 2 to 10%, 2 to 7%, or 2 to 5% wt. of binder. In some embodiments, the printed matrix comprises >0 to 50% wt, 10% to 45%, 20% to 45%, 25-40% wt of binder. In some embodiments, binder is absent from the printing fluid or absent from the bulk material.

Suitable binders include water-soluble synthetic polymer, carboxymethylcellulose, hydroxypropylcellulose, polyvinly pyrrolidone, hydroxypropylmethylcellulose, Sorbitol, mannitiol. Xylitol, lactitol, erythritol, pregelatinized starch, modified starch, arabinogalactan. Preferred binders include polyvinylpyrrolidone (povidone), mannitol, hydroxypropyl cellulose, or a combination thereof.

4. Surfactants

Solid oral dosage formulations of the present invention may comprise one or more surfactants. The surfactants may be including in the inventive formulations to increase the rate of disintegration of the solid oral dosage once it contacts the inside of the mouth of the recipient and/or is further ingested by the patient. The inventive solid dosage formulation may include at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Some embodiments of the invention include solid formulations wherein: a) the at least one surfactant is present in an amount ranging from 0.5-7.0% wt. based upon the final weight of the dosage form; b) the at least one sweetener is present in an amount range from 0.01-2.0% based upon the final weight of the dosage form; c) the at least one binder is present in an amount range from 5-15% based upon the final weight of the dosage form; d) the at least one disintegrant is present in an amount range from 10-30% based upon the final weight of the dosage form; and/or e) the at least one glidant is present in an amount range from 0-2% based upon the final weight of the dosage form.

Suitable surfactants for use in the solid oral dosage formulations of the present disclosure include one or more surfactants and/or co-surfactants of Formula I,

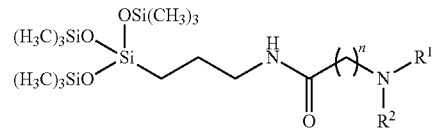

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

The concentration of the surfactant system in the solid oral dosage formulation should be sufficient to provide a formulation that can be readily manufacture, stored, and administered to a human or an animal patient.

In printed solid formulations the inclusion of a surfactant in the printing fluid, bulk powder and Active-containing particles aids in ensuring rapid dispersion of the 3DP dosage form when placed in a minimal amount of water. The surfactant may serve to enhance wetting of the particles. The surfactant need only be present in an amount sufficient to enhance dispersion as compared to another 3DP dosage form formulated without the surfactant. If the surfactant is present in too high of an amount, however, it may negatively impact mouth feel, performance and/or physical properties of the dosage form. The surfactant can be included in the Active-including granule, bulk powder and/or printing fluid. In some embodiments, the total amount of surfactant present in the drug-containing particles ranges from about 0-5%, >0-5%. 1-4.2%, 2-3% wt. based upon the weight to the drug-containing particles. In some embodiments, the amount of surfactant present in the bulk powder, excluding the Active-containing particles, ranges from about 0-5%, >0-5%. 1-4.2%, 2-3% wt., based upon the weight to the bulk powder.

5. Disentegrants

Disintegrents are a type of excipient added to solid formulation to adjust the physical properties of the formulation. Many solid formulations include at least one binder and at least one disintegrant, key ingredients for controlling the hardness, friability and dispersion time of the matrix. Generally, the greater the amount of binder, the higher the hardness, the lower the friability and the slower the dispersion time of the solid formulation. On the other hand, increasing the amount of disintegrant provides lower hardness, increased friability and a faster dispersion time. Accordingly, the solid formulation may comprise balanced amounts of binder and disintegrant.

Suitable disintegrants include microcrystalline cellulose (MCC), croscarmellose (cross-linked carboxymethylcellulose), powdered cellulose or a combination thereof. Preferred disintegrants include microcrystalline cellulose, e.g. AVICEL® PH 101, a combination of two grades of microcrystalline cellulose, and croscarmellose. Suitable grades of AVICEL® are summarized in the table below. The dosage form can comprise one or a combination of the specified grades. All Such embodiments containing single grades or a combination of grades are contemplated.

In the case of a solid formulation formed by printing a matrix of components, the formulation may include one or more disintegrants can be included in the printed matrix. The disintegrant can be present in the bulk powder and/or drug-containing particles. The disintegrant is independently selected upon each occurrence. In some embodiments, the bulk powder comprises 3-20% wt, 3-15% wt., 4-12% wt. or 10-16% wt. of disintegrant. In some embodiments, the drug containing particles comprise 15-35% wt., 20-30% or 25-30%% wt of disintegrant.

6. Sweeteners

A sweetener is a type of excipient that may be added to a formulation to alter its organoleptic properties. One or more sweeteners can be included a solid formulation, for example a solid formulation comprising a printed matrix. The sweetener can be present in the bulk powder, drug-containing particles and/or in a fluid, such as a printing fluid used to form the solid. In formulations formed by printing solid matrices better taste-masking is observed when at least one sweetener is present in at least the printing fluid. The sweetener may be independently selected upon each occurrence. The printing fluid, drug-containing particles and/or the bulk powder can have at least one Sweetener in common. In some embodiments, the bulk powder comprises >0 to 5% wt. %, or >0 to 2% wt., or >0 to 1.5% wt. of Sweetener. In some embodiments, the printing fluid comprises >0 to 5% wt., >0 to 4% wt., >0 to 3% wt., >0 to 2% wt., 0.1 to 5% wt. %, 0.1 to 4% wt., 0.1 to 3% wt., 0.1 to 2% wt., 0.5 to 3% wt., or 1 to 3% wt. sweetener. In some embodiments, the drug-containing particles comprise 0-5% wt. of sweetener.

Suitable sweeteners may be selected from the group consisting of glycyrrhizinic acid derivative, e.g. magnasweet (monoammonium glycyrrhizinate). Sucralose and a combination thereof. The preferred sweetener in the printing fluid is sucralose. Sweetener is present in at least the printing fluid but may also be present in the bulk powder.

7. Flavorants

A flavorant is a type of excipient that may be added to a formulation to alter its organoleptic properties One or more flavorants can be included in the matrix. The flavorant can be present in the bulk powder, drug-containing particles, and/or the printing fluid. The flavorant is preferably water soluble, aqueous fluid soluble, partially water soluble or partially aqueous fluid soluble. If present in the bulk powder, the flavorant is preferably present in a form applied to a carrier powder before preparation of the bulk powder. Suitable carrier powders may include starches, modified starches, celluloses, and other powder capable of absorbing, adsorbing, encasing, or encapsulating the flavorant. In some embodiments, the printing fluid comprises 0-5% wt., 0.01-1.0% wt. or 0.05-0.5% wt. of flavorant. In some embodiments, the bulk powder comprises 0.1 to 10% wt, or 1 to 10% wt., 2 to 8% wt. 3-7% wt. of flavorant-incorporated carrier powder. In some embodiments, the printed matrix comprises 0-10% wt., 0.01-10% wt. of flavorant. In some embodiments, the flavorant is absent from the printing fluid or absent from the bulk material. Suitable flavorants include peppermint, spearmint, mint, vanilla, orange, lemon, citrus, lime, grape, cherry, Strawberry, chocolate, coffee or a combination thereof.

II. Method of Making Solid Formulations

Tablets that include at least one active may be manufactured by any means known in the art. Exemplary methods include, direct compression, dry granulation, and wet granulation. Steps in these processes may include any of the following steps practiced in an order known in the industry. These steps include mixing of solid ingredients with one another or with liquids in amounts small enough to form a final dry formulation. Another commonly used step is granulation, a processes commonly used to create particles of a uniform and ideally similar size and shape. Depending upon the formulation the granulation step may be practiced on individual components of the final formulation, mixtures of the components of the final formulation, or on the final formulation.

If the process of creating a solid formulation includes the step of first creating a liquid, gel, or paste or if the formulation includes the step of mixing at least one solid ingredient with at least one liquid ingredient the process of forming a tablet is likely to include the step of drying the formulation. Suitable drying process will depend on the components of the formulation and desired final product. Suitable drying processes include, vacuum drying, spray drying, fluid bed drying, freeze drying, pan or tray drying and any method known in the art. Conventional means known in the art for creating tablets include compressing mixtures that include the desired final composition of the formulation. Machines commonly used for form tablets include stamping and rotary presses. Generally, tablets are sized and shaped, so as to facilitate oral administration to an attended patient population.

Still another exemplary method for formulating a tablet includes 3-dimensional printing of matrices that include at least one Active. A summary of some of some variants of this process may be found in the Examples section.

III. Liquid Formulations

Liquid formulations may include formulations made with a liquid Active ingredient, an Active ingredient dissolved in a suitable solvent for example water, an Active ingredient formulated in a gel or a paste, or an Active ingredient in the form of a particle suspended in a liquid, paste, lotion or ointment.

IV. Emulsions that Include at Least One Active

Some compounds useful in healthcare applications are not particularly soluble in solvents suitable for use in, or on, human or animal patients, moreover some compounds useful in cleansing formulation of particular use in healthcare applications may not be very soluble in solvents otherwise of utility in such applications. Some such compounds may be formulated in emulsions, which are suitable for use in healthcare applications.

Emulsions that include Actives may be used as or included in topicals intended for application directly on patients, including, but limited to the following; salves, ointments, suppositories, lotions, drops, and scrubs. Actives may be formulated in emulsions that may be administered to a patient orally, anally, or by aspiration. Actives may be formulated in emulsions suitable for intravenous or parenteral administration.

Actives may also be encapsulated, once encapsulated the Active may be formulated in a liquid suspension, for use topically, and/or internally in a patient.

Useful emulsion formulations must be physically stable. The droplet size limits defined in USP <729> generally apply throughout the assigned shelf life. All true emulsions are thermodynamically unstable and may over time undergo a range of processes which tend to increase the droplet size. These include direct droplet coalescence, when two droplets collide and form a single new droplet, and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Emulsion formulations must also be chemically stable. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants may lower pH, which may then promote further degradation. Thus, pH should be controlled during manufacture and parenteral emulsion formulations may include a buffering agent to provide additional control. Any decrease in pH over the assigned shelf-life may be indicative of chemical degradation.

In some aspects of the invention, emulsion formulations are prepared and characterized to identify formulations and processes that will allow an Active to be incorporated into an emulsion for intradermal administration and to remain stable during the shelf life of the formulation.

In one embodiment, the composition is a stable system maintaining an intensity-weighted mean particle size as determined by dynamic light scattering (DLS) of about 50 nm to 1000 nm, 50 to 500 nm, 50 nm to 400 nm, 50 nm to 300 nm, 50 nm to 200 nm or 50 nm to 100 nm. In another embodiment, the average droplet size is maintained below 500 nm for a period of at least 1 month, 3 months, 6 months, 9 months, 12 months, 2 years or 3 years at room temperature.

In another embodiment, the average droplet size is maintained below 500 nm for a period of at least 1 month, 3 months, 6 months, 9 months, 12 months, 2 years or 3 years at 5° C.

Some aspects provide an emulsion suitable for parenteral administration. Some aspects provide an emulsion suitable for intravenous administration. Some aspects provide an emulsion suitable for subdermal and/or subcutaneous administration.

1. Active

Some stable pharmaceutical compositions which include at least one Active also include, a surfactant or mixtures of surfactants, a co-surfactant, an oil, with an aqueous phase. The composition is in the form of an oil-in-water emulsion which remains stable over an extended period of time and which is suitable for dilution and intravenous administration.

2. Non-Aqueous Phase

The Active may be present in the oil phase with an emulsifier, a co-emulsifier and an oil. The oil phase is then combined with an aqueous phase comprising water and a tonicity agent as described below to generate the stable emulsion. In some formulation the oil phase will have an oil which includes at least one Active in a ratio of about 13:1. Use of this ratio may produce, when mixed with the water phase, an emulsion which is more stable as compared to an emulsion in which the oil phase contains an oil:Active ratio of less than about 12:1 or 11:1, and/or greater than about 15:1, 20:1, or 11:1, and/or greater than about 15:1, 20:1, or 30:1.

The oil (hydrophobic) phase comprises an oil. Triglycerides are exemplary oils for use in the compositions described herein. In certain embodiments the oil is or comprises a vegetable oil. "Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used. Exemplary vegetable oils include but are not limited to almond oil, babassu oil, black currant seed oil, borage oil, canola oil, castor oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil is or comprises safflower oil, sesame oil, corn oil, olive oil and/or soybean oil. In more specific embodiments, the oil is or comprises safflower oil, and/or soybean oil. The oil is present in the emulsion at about 9 wt/wt %, though this may vary between about 5 wt./wt. % to 12 wt./wt % or 9 wt./wt. % to 10 wt./wt. %.

3. Aqueous Phase

The aqueous phase of the Active emulsion can be a mixture of water and a tonicity agent, including those such as but not limited to sucrose, mannitol, glycerin or dextrose or a mixture thereof. Also included in the aqueous phase is a pH-modifying agent. Sodium oleate may be used in some of the inventive examples to adjust the pH of the emulsion to about 6 to 9, depending on the desired emulsion formulation. The aqueous phase is produced by mixing water with the tonicity agent and sodium oleate as the pH modifying agent. Other pH modifiers that may be used include but are not limited to sodium hydroxide, potassium hydroxide, magnesium hydroxide, Tris, sodium carbonate and sodium linoleate. The pH modifier used is effective for adjusting the pH of the emulsion to a preferred pH of about 6 to 9, 7 to 8, or about 6, 7, 8 or 9. The aqueous phase can readily form by mixing at room temperature.

The aqueous phase may further contain a buffering agent to promote stability of the emulsion formulation. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and emulsion formulations may include a buffering agent to provide additional control. Any decrease in pH over the assigned shelf-life may be indicative of chemical degradation.

4. Buffers

Suitable buffers are well known to the person skilled in the art and include but are not limited to a phosphate buffer, citrate buffer, Tris buffer, carbonate buffer, succinate buffer, maleate buffer or borate buffer. Tris buffer is used in some exemplary formulations the pH of the emulsion may be adjusted to about 8 to 9. In a particular embodiment, the buffer is selected from the group, phosphate buffered saline (PBS), modified PBS (PBS-mod) and citrate buffer. In some embodiments, the aqueous phase comprises a buffer, that when mixed with the oil phase will provide a substantially isotonic oil in water emulsion.

Buffering agents useful for the presently described compositions include, but are not limited to, a phosphate buffer, citrate buffer, Tris buffer, carbonate buffer, succinate buffer, maleate buffer or borate buffer. In a particular embodiment, the buffer is selected from the group, phosphate buffered saline (PBS), modified PBS (PBS-mod) and citrate buffer. In some embodiments, the aqueous phase comprises a buffer, that when mixed with the oil phase will provide a substantially isotonic oil in water emulsion. In some embodiments, when the aqueous phase contains a buffering agent, the aqueous phase does not include a tonicity agent. Also, when a buffer is added to the aqueous phase, a pH-adjusting agent may not be added to the aqueous phase. It is understood that a buffer can be added to the aqueous phase or the buffer can be added to the emulsion.

5. Tonicity Agents

In some embodiments, the aqueous phase contains a tonicity agent such as sucrose. The tonicity agent is added to an aqueous phase having about 0% to 30%, 0% to 25% or about 20% of the tonicity agent (wt./wt.). It was surprisingly found that a composition containing about 20% sucrose wt./wt. in the aqueous phase produced an emulsion that was particularly stable as determined by freeze-thaw testing. Accordingly, preferred embodiments include an emulsion in which the aqueous phase comprises a tonicity agent which imparts greater chemical and/or physical stability as compared to an emulsion wherein the aqueous phase contains less than about 10%, 15% or 20% wt./wt. tonicity agent or more than about 30%, 40% or 50% wt./wt. tonicity agent.

In some formulations, the aqueous phase further comprises dexamethasone sodium phosphate (also referred to as "dexmethasone phosphate"). Dexamethasone sodium phosphate is a corticosteroid which is freely soluble in water. Daily dosages for dexamethasone sodium phosphate range from about 0.5 mg to 20 mg, more preferably from about 14 mg to 18 mg or 16 mg, depending on the severity of the disease or disorder. Accordingly, an Active emulsion further comprising dexamethasone may contain dexamethasone sodium phosphate in the aqueous phase. Accordingly, the aqueous phase of an emulsion suitable for intravenous administration may contain about 0.5 mg to 20 mg, 14 mg to 18 mg or about 16 mg dexamethasone sodium phosphate.

In some formulations. a solution of dexamethasone sodium phosphate can be mixed into the fine emulsion prior to sterile filtration to prepare an emulsion containing dexamethasone sodium phosphate in the aqueous phase.

Some methods of making emulsions suitable for intravenous administration.

Such formulations may be made in conformity with conventional aseptic methods used to prepare Actives intended for subdermal administration.

6. Preservatives

Preservative that may be added to any of the liquid formulations disclosed herein include, bactericides, fungicides, and antioxidants.

7. Surfactants

The emulsion may comprise at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof.

Suitable surfactants for use in the conditioner formulations of the present disclosure include one or more surfactants and/or co-surfactants of Formula I,

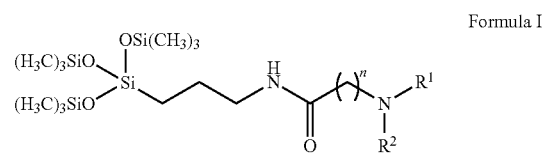

Formula I wherein R1 and R2 may be the same or different, and comprise at least one group selected from the group consisting of C1-C6 alkyl, optionally the C1-C6 alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with R3, wherein R3 is selected from the group consisting of hydrogen, oxygen, hydroxyl, and $C_1$-$C_6$ alkyl; and an optional counterion associated with the compound which, if present, is selected from the group consisting of chloride, bromide, and iodide.

In particular, suitable surfactants or co-surfactants may include one or more of any of Surfactants 1-6 described herein.

V. Method of Making an Emulsion

In one such formulation exemplary emulsion, an aqueous phase is combined with the oil phase, under high-speed homogenization to produce a coarse emulsion. As described in Examples 1, 2, 3, 4, 5 and 6, the combined aqueous and oil phases is homogenized using an IKA Ultra-Turrax T25 dispersing instrument at a speed of 20,000 rpm for 1 min. The speed used in this first homogenization step may vary, for example, from 2000 rpm to 25,000 rpm, or from 15,000 rpm to 22,000 rpm. The time of the homogenization step can also vary, for example, from 0.5 min to 1 hour, or from 1 min to 45 min. This crude emulsion is then homogenized into a fine emulsion by a high-pressure homogenizer, which may be a microfluidizer. The interaction chamber and the cooling coil portions of the microfluidizer are cooled by water, such as by an ice bath. The temperature of the ice bath may be between about 0° to 10° C., or about 2 to 6° C. The temperature of the emulsion coming out of the high-pressure homogenization may be between about 0° to 60° C., 15° C., to 60° C., 20° C. to 40° C., or at about 25° C. The microfluidizer is first primed with water, then the crude emulsion is introduced. The output from the homogenizer is initially run to waste to remove priming water, and priming water and emulsion mixtures, and then collected in a clean vessel when the stream becomes consistent in appearance. The high-pressure homogenizer cycle may be repeated to sufficiently reduce oil droplet size. The pressure used for the homogenization may vary. The pressures may be between 40 5000 and 30,000 psi. The number of passes through the microfluidizer may vary in order to achieve the desired droplet size. The number of passes may be from about 2 to 20, 2 to 15, 4 to 15, 4 to 12 or 7 to 8.

The pharmaceutical formulation may then be passed through a filter system at room temperature, and/or autoclaved, to achieve sterilization. The filters used to achieve sterilization may be chosen by the skilled artisan and may have a nominal pore size of 0.2 μm. The filter material used may vary. In one embodiment, the filter is nylon. In another embodiment, the filter is a Posidyne® filter (covalent charge-modified Nylon 6,6 membrane which exhibits a net positively-charged zeta potential in aqueous solutions). For large scale production the method above may need to be modified. A skilled practitioner could combine these materials in a different order and using different processing equipment to achieve the desired end result.

In one embodiment of the disclosure, the homogenization can be done in repeated cycles to achieve an emulsion in which the oil particle/globule size is less than 2 microns (μm) with intermediate cooling of the homogenized product to a temperature less than about 25° C.

The final emulsion comprises an oil portion (oil phase) dispersed in an aqueous portion (aqueous phase). The ratio of components to the Active within the oil phase is an important characteristic of the emulsion which may affect stability of the formulation prepared for injection. As described herein, the oil phase comprises The Active, an oil and an emulsifier, examples of which are provided herein.

In some formulations the final Active emulsion contains 0.7 wt./wt. % Active but may range from about 0.2 wt./wt. % to 1.5 wt./wt. %, 0.4 wt./wt. % to 1.0 wt./wt. % or 0.6 wt./wt. % to 0.7 wt./wt. %. An emulsion is prepared which contains about 130 mg Active, however, preparations may also be prepared according to the present disclosure which contain about 100 mg to 1000 mg, 100 mg to 500 mg, 250 mg to 750 mg or 100 to 200 mg of the Active.

In one embodiment, the ratio of oil:Active (wt. %:wt. %) within the oil phase ranges from about 11:1 to 15:1, 12:1 to 14:1, 13:1 to 13.5:1, 13:1 to 14:1, or 12:1 to 15:1. In another embodiment, the ratio of oil:Active is about 11:1, 11.5:1, 12:1, 12.5:1, 13:1, 13.5:1, 14:1, 14.5:1 or 15:1.

The ratio of emulsifier to Active may also vary. For example, the ratio of emulsifier:Active (wt. %:wt. %) within the oil portion ranges from about 15:1 to 30:1, 20:1 to 25:1, 18:1 to 22:1 or 10:1 to 30:1. In one embodiment, the emulsifier:Active (wt. %:wt. %) is about 15:1, 18:1, 19:1, 20:1, 21:1, 22:1 or 23:1.

The ratio of components within the oil phase may alternatively be expressed in the ratio of (emulsifier plus oil):Active (wt. %:wt. %). Ratios envisioned in the present disclosure may range from about 20:1 to 40:1, 25:1 to 35:1, 30:1 to 35:1 or 33:1 to 37:1, or may be, for example, about 30:1, 32:1, 33:1, 34:1, 35:1, 36:1, 37:1, 38:1 or 40:1.

VI. Formulations for Intravenous Perfusion

Intravenous emulsions often have a very small droplet size to in order to enable them to circulate in the bloodstream without causing capillary blockage and embolization. These size limits are typified by USP33-NF28 General Chapter <729> for Globule Size Distribution in Lipid Injectable Emulsions, hereinafter referred to as USP <729>, which defines universal limits for (1) mean droplet size not exceeding 500 nm or 0.5 μm and (2) the population of large-diameter fat globules, expressed as the volume-weighted percentage of fat greater than 5 μm (OFAT5) not exceeding 0.05%, irrespective of the dinal lipid concentration.

Some aspects of the invention relates to formulations suitable for healthcare applications, comprising an Active in the form of a base or in the form of a salt of an acid which is pharmaceutically acceptable, solubilized in a mixture of an alcohol and at least one surfactant, in some formulations the surfactant may include Macrogol 15 hydroxystearate and/or the inventive surfactants disclosed herein in a surfactant/alcohol ratio by weight ranging from 25/75 to 80/20, prefer ably from 73/27 to 77/23. 0012. In some embodiments the Active may be solubilized in a mixture of ethanol and of a surfactant comprising a mixture of the polyethoxylated monoester and diester of 12-hydroxystearic acid described hereinafter.

1. Solvents

Solvent suitable for liquid formulations are any liquids recognized as safe and effective for ingestion, application, or injection into a patient, or onto the surface of a human or an animal patient. It being understood in the art that some solvents when present in small amounts in a formulation are suitable for use the inventive formulations irrespective of their known or unknown toxicity if administered to a patient at a higher concentration. Commonly used solvents include liquids that have been designated by Generally Regarded as Safe (GRAS) by the United States Food and Drug Administration. Some suitable solvent include, but are not limited to, water: alcohols, and glycerol.

2. Surfactants

In some formulations the surfactant comprises, by weight, from about 35% to about 55% of monoester and diester and from about 30% to about 40% of polyethylene glycol H(OCHCH), OH and additional surfactants. It comprises, by weight, as main components, from 35% to 55% of monoester and diester and from 30% to 40% of polyethylene glycol H(OCH2CH2), OH, and optionally other compounds making up the rest to 100%. It comprises, by weight, from 10% to 20% of monoester, from 25% to 35% of diester and from 30% to 40% of polyethylene glycol H(OCH$_2$CH)—OH and also other compounds making up the rest to 100%.

The surfactants/ethanol ratio ranges from 73/27 to 77/23 and the concentration of compound of formula (I) ranges from 5 to 25 mg/ml.

The pharmaceutical formulation may be intended to be diluted so as to form perfusion solutions.

V. Methods for Making a Healthcare Perfusions

Some aspects of the invention include methods for formulating at least one Active for use in a formulation that may be administered to a human or to an animal by perfusion. Such methods may include at least some of the following steps: heating at least one surfactant until it becomes a liquid/and or adding a surfactant that is a liquid at room temperature or that is suitably soluble in a suitable solvent at room temperature; adding at least one alcohol; if necessary, cooling the mixture to ambient temperature, adding at least one Active to the formulation; and sterilizing the formulation, by for example, filtration.

Some aspects of the invention also relate to a perfusion solution comprising at least one Active in the form of a base or in the form of a salt of an acid which is pharmaceutically acceptable, obtained by diluting 1 Volume of the pharmaceutical solution in 20 to 500 volumes of an isotonic solution. In some formulations the Active is present at a concentration ranging from 0.01 to 1.2 mg/ml, the surfactants at a concentration ranging from 0.48 to 37 mg/ml and the ethanol at a concentration ranging from 0.35 to 35 mg/ml are diluted in the isotonic solution. The perfusion solution is intended to be administered to a human being or to an animal.

Some aspects of the invention relate to methods for preparing the perfusion solution, consisting in diluting 1 Volume of the pharmaceutical solution in 20 to 500 volumes of the isotonic solution.

In some aspects of the invention, the pharmaceutical formulation may comprise at least one other additive customarily used in liquid pharmaceutical formulations. It may, for example, be an antioxidant, a preservative, a buffer, etc. According to another embodiment of the invention, the pharmaceutical formulation comprises only the surfactant, the alcohol and the Active.

Surfactants

Heath care formulations may include one or more surfactants chosen from one or more surfactant classes, collectively referred to as the surfactant system. The surfactant system functions as an emulsifier for the O/W emulsion.

Suitable surfactants for use in the inventive healthcare formulations of the present disclosure include one or more surfactants and/or co-surfactants of Formula I,

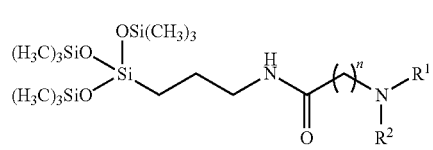

Formula I wherein $R1$ and $R2$ may be the same or different, and comprise at least one group selected from the group consisting of C1-C6 alkyl, optionally the C1-C6 alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with R3, wherein R3 is selected from the group consisting of hydrogen, oxygen, hydroxyl, and C1-C6 alkyl; and an optional counterion associated with the compound which, if present, is selected from the group consisting of chloride, bromide, and iodide.

In particular, suitable surfactants or co-surfactants may include one or more of any of Surfactants 1-6 described herein.

The amino acid may be naturally occurring or synthetic or may be derived from a ring opening reaction of a lactam, such as caprolactam. The ring-opening reaction may be either an acid or alkali catalyzed reaction, and an example of an acid catalyzed reaction is shown below in Scheme 1.

SCHEME 1

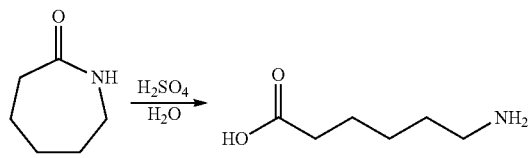

The amino acid may have as few as 1 or as many as 12 carbons between the N- and C-terminii. The alkyl chain may be branched or straight. The alkyl chain may be interrupted with nitrogen, oxygen, or sulfur. The alkyl chain may be further substituted with one or more substituents selected from the group consisting of hydroxyl, amino, amido, sulfonyl, sulfonate, carboxyl, and carboxylate. The N-terminal nitrogen may be acylated or alkylated with one or more alkyl groups. For example, the amino acid may be 6-(dimethylamino)hexanoic acid.

The siloxane may be substituted with one or more alkoxy groups, such as methoxy, ethoxy, isopropoxy, tertiary butoxy, and others. The siloxane may be further substituted with one or more alkyl groups, such as propyl, wherein the alkyl group may yet be further substituted with an appropriate functional group to permit coupling of the siloxane to the amino acid, such as a nitrogen. For example, the siloxane may be 3-aminopropyltris(trimethylsiloxy)silane.

The siloxane derivative of the amino acid may be synthesized as shown below in Scheme 2. As shown, 6-aminohexanoic acid is treated with formaldehyde in formic acid at reflux to give 6-(dimethylamino)hexanoic acid. The free carboxylic acid is then coupled to 3-aminopropyl(trismethylsiloxy)silane in refluxing toluene to give the desired siloxane derivative.

SCHEME 2

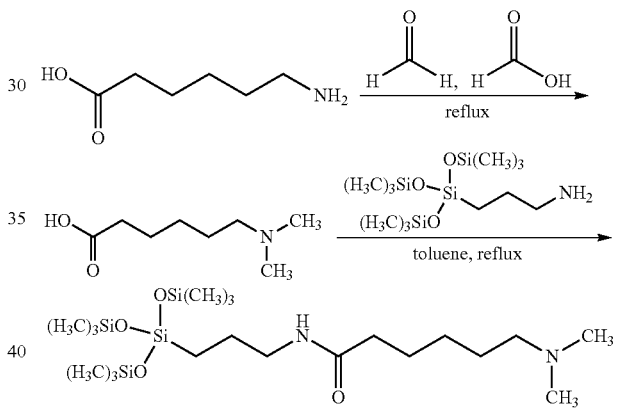

The N-terminal nitrogen may be further derivatized to modify or improve water solubility and surface-active properties. A sample synthetic scheme is shown below in Scheme 3, in which the N-terminal nitrogen is treated with hydrochloric acid to give the corresponding hydrochloride salt.

SCHEME 3

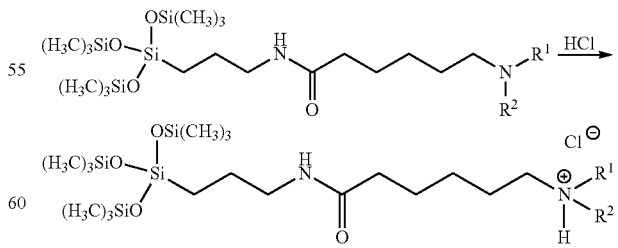

The N-terminal nitrogen may be alkylated. A sample synthetic scheme is shown below, in which the N-terminal nitrogen is treated with methyl iodide to give the corresponding quaternary amine salt.

SCHEME 4

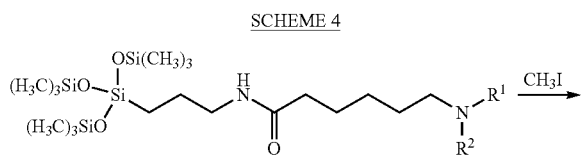

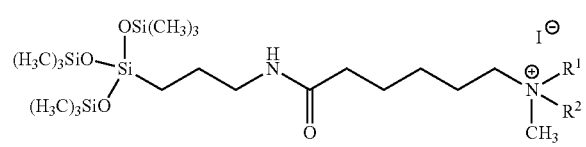

The N-terminal nitrogen may be treated with hydrogen peroxide in water at reflux to give the corresponding N-oxide, as shown in the sample synthetic scheme below, Scheme 5.

SCHEME 5

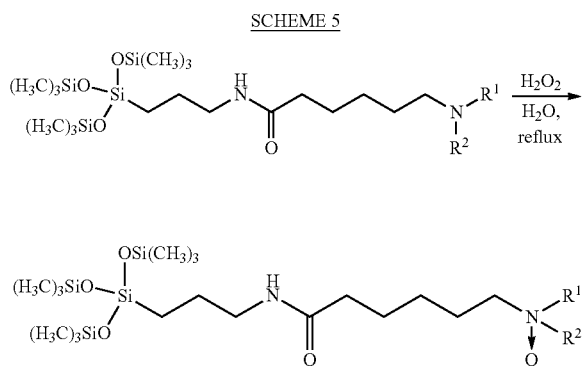

The compounds of the present disclosure demonstrate surface-active properties. These properties may be measured and described by various methods. One method by which surfactants may be described is by the molecule's critical micelle concentration (CMC). CMC may be defined as the concentration of a surfactant at which micelles form, and above which all additional surfactant is incorporated into micelles.

As surfactant concentration increases, surface tension decreases. Once the surface is completely overlaid with surfactant molecules, micelles begin to form. This point represents the CMC, as well as the minimum surface tension. Further addition of surfactant will not further affect the surface tension. CMC may therefore be measured by observing the change in surface tension as a function of surfactant concentration. One such method for measuring this value is the Wilhemy plate method. A Wilhelmy plate is usually a thin iridium-platinum plate attached to a balance by a wire and placed perpendicularly to the air-liquid interface. The balance is used to measure the force exerted on the plate by wetting. This value is then used to calculate the surface tension ($\gamma$) according to Equation 1:

$$\gamma = F/l \cos \theta \qquad \text{Equation 1:}$$

wherein l is equal to the wetted perimeter (2w+2d, in which w and d are the plate thickness and width, respectively) and cos θ, the contact angle between the liquid and the plate, is assumed to be 0 in the absence of an extant literature value.

Another parameter used to assess the performance of surfactants is dynamic surface tension. The dynamic surface tension is the value of the surface tension for a particular surface or interface age. In the case of liquids with added surfactants, this can differ from the equilibrium value. Immediately after a surface is produced, the surface tension is equal to that of the pure liquid. As described above, surfactants reduce surface tension; therefore, the surface tension drops until an equilibrium value is reached. The time required for equilibrium to be reached depends on the diffusion rate and the adsorption rate of the surfactant.

One method by which dynamic surface tension is measured relies upon a bubble pressure tensiometer. This device measures the maximum internal pressure of a gas bubble that is formed in a liquid by means of a capillary. The measured value corresponds to the surface tension at a certain surface age, the time from the start of the bubble formation to the occurrence of the pressure maximum. The dependence of surface tension on surface age can be measured by varying the speed at which bubbles are produced.

Surface-active compounds may also be assessed by their wetting ability on solid substrates as measured by the contact angle. When a liquid droplet comes in contact with a solid surface in a third medium, such as air, a three-phase line forms among the liquid, the gas and the solid. The angle between the surface tension unit vector, acting at the three-phase line and tangent at the liquid droplet, and the surface is described as the contact angle. The contact angle (also known as wetting angle) is a measure of the wettability of a solid by a liquid. In the case of complete wetting, the liquid is completely spread over the solid and the contact angle is 0°. Wetting properties are typically measured for a given compound at the concentration of 1-100×CMC, however, it is not a property that is concentration-dependent therefore measurements of wetting properties can be measured at concentrations that are higher or lower.

In one method, an optical contact angle goniometer may be used to measure the contact angle. This device uses a digital camera and software to extract the contact angle by analyze the contour shape of a sessile droplet of liquid on a surface.

Potential applications for the surface-active compounds of the present disclosure include formulations for use as shampoos, hair conditioners, detergents, spot-free rinsing solutions, floor and carpet cleaners, cleaning agents for graffiti removal, wetting agents for crop protection, adjuvants for crop protection, and wetting agents for aerosol spray coatings.

It will be understood by one skilled in the art that small differences between compounds may lead to substantially different surfactant properties, such that different compounds may be used with different substrates, in different applications.

The following non-limiting embodiments are provided to demonstrate the different properties of the different surfactants. In Table 1 below, short names for the surfactants are correlated with their corresponding chemical structures.

TABLE 1

| Surfactant | Formula & Name |
|---|---|
| Surfactant 1 | 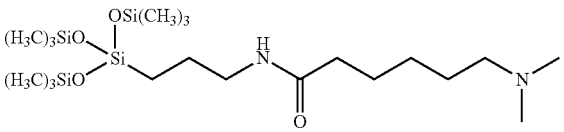<br>6-(dimethylamino)-N-(3-(1,1,1,5,5,5-hexamethyl-3-((trimethylsilyl)oxy)trisiloxan-3-yl)propyl)hexanamide |
| Surfactant 2 | 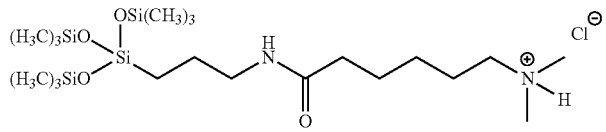<br>6-((3-(1,1,1,5,5,5-hexamethyl-3-((trimethylsilyl)oxy)trisiloxan-3-yl)propyl)amino)-N,N-dimethyl-6-oxohexan-1-aminium chloride |
| Surfactant 3 | 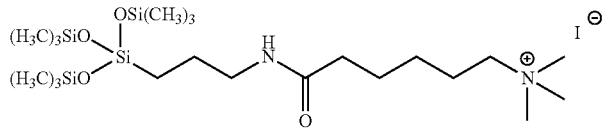<br>6-((3-(1,1,1,5,5,5-hexamethyl-3-((trimethylsilyl)oxy)trisiloxan-3-yl)propyl)amino)-N,N,N-trimethyl-6-oxohexan-1-aminium iodide |
| Surfactant 4 | 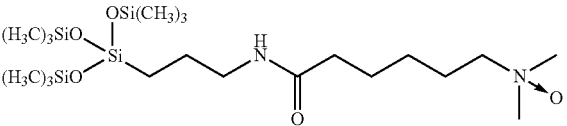<br>6-((3-(1,1,1,5,5,5-hexamethyl-3-((trimethylsilyl)oxy)trisiloxan-3-yl)propyl)amino)-N,N-dimethyl-6-oxohexan-1-amine oxide |
| Surfactant 5 | 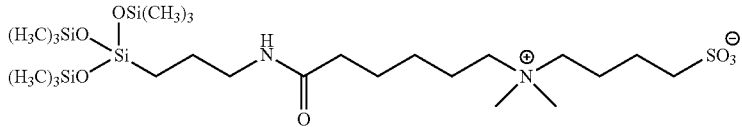<br>4-((6-((3-(1,1,1,5,5,5-hexamethyl-3-((trimethylsilyl)oxy)trisiloxan-3-yl)propyl)amino)-6-oxohexyl)dimethylammonio)butane-1-sulfonate |

Each of the five compounds are effective as surface-active agents, useful for wetting or foaming agents, dispersants, emulsifiers, and powders, foams, among other applications.

Surfactants 1 and 2 candidates may be used in a variety of healthcare products for example as foaming or wetting agents.

Surfactant 3 is cationic. These surfactants are useful in both the applications described above and some further special applications such as surface treatments used on surfaces that may contact a patient or objects that may contact a patient these surfactants can also be used to generate water repellant surfaces which may find utility in wound dressings, bandages and the like.

Surfactant 4 is non-ionic, and can be used in healthcare formulations, and a variety of formulations including emulsions and/or suspensions that include Actives.

Surfactant 5 is zwitterionic. These surfactants may be useful as co-surfactants in all of the applications described above.

The amount of the compounds disclosed herein used in a formulation may be as low as about 0.001 wt. %, about 0.05 wt. %, about 0.1 wt. %, about 0.5 wt. %, about 1 wt. %, about 2 wt. %, or about 5 wt. %, or as high as about 8 wt. %, about 10 wt. %, about 15 wt. %, about 20 wt. %, or about 25 wt. %, or within any range using any two of the foregoing values.

EXAMPLES

Nuclear magnetic resonance (NMR) spectroscopy was performed on a Bruker 500 MHz spectrometer. The critical micelle concentration (CMC) was determined by the Wilhelmy plate method at 23° C. with a tensiometer (DCAT 11, DataPhysics Instruments GmbH) equipped with a Pt—Ir plate. Dynamic surface tension was determined with a bubble pressure tensiometer (Krüss BP100, Krüss GmbH), at 23° C. Contact angle was determined with the optical

Example 1a

Synthesis of 6-(dimethylamino)-N-(3-(1,1,1,5,5,5-hexamethyl-3-((trimethylsilyl)oxy)trisiloxan-3-yl)propyl)hexanamide (Surfactant 1) and 6-((3-(1,1,1,5,5,5-hexamethyl-3-((trimethylsilyl)oxy)trisiloxan-3-yl)propyl)amino)-N,N-dimethyl-6-oxohexan-1-aminium salt (Surfactant 2)

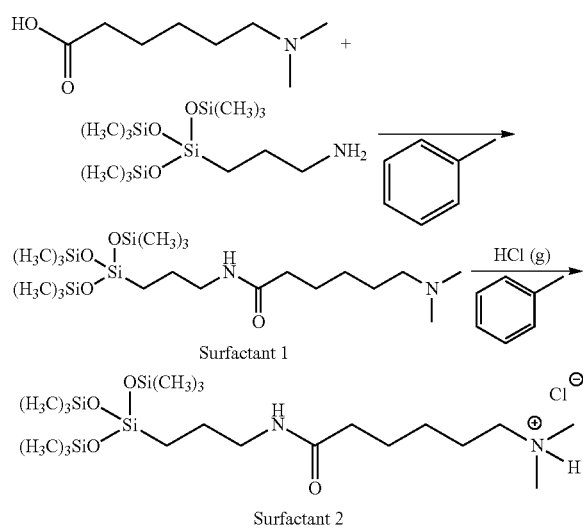

(2) 6-(Dimethylamino)hexanoic acid (2.00 g, 12.56 mmol, 1 equiv.) was dissolved in toluene (50 mL) in a 100 mL round bottom boiling flask equipped with a Dean Stark trap, then 3-aminopropyltris(trimethylsiloxy)silane (5.48 mL, 13.81 mmol, 1.1 equiv.) was added. The reaction vessel was heated, and the reaction refluxed for 24 hours until no more water separated in the Dean Stark tube. The solvent was removed under vacuum to give Surfactant 1 as a yellow oil in 94% yield. $^1$H NMR (500 MHz, DMSO) δ: 0.09 (s, 27H), 0.28-0.31 (m, 2H), 1.12-1.26 (m, 2H), 1.27-1.30 (m, 4H), 1.38-1.41 (m, 2H), 1.94 (t, J=7.3 Hz, 2H), 2.00 (s, 6H), 2.06-2.03 (m, 2H), 2.89 (dd, J=12.9, 6.8 Hz, 2H).

In its neutral form, Surfactant 1 is slightly soluble in pure water without addition of hydrotropes or other surfactants, but after protonation in slightly acidic conditions it becomes interfacially active (Surfactant 2). The acidic conditions can be generated by the addition of any acid or acidic buffer in the pH range of 4-7. Surfactant 2 can also be prepared in non-aqueous solutions, for example by sparging gaseous HCl in toluene in the presence of Surfactant 1.

Example 1b

Determination of Critical Micelle Concentration (CMC) of Surfactant 2

The critical micelle concentration (CMC) for Surfactant 2 was tested with a chloride counterion and was determined to be about 2 mmol. The plateau value of minimum surface tension that can be reached by this surfactant is about 23 mN/m. FIG. 1 is a plot of these results, showing surface tension versus concentration.

Example 2a

Synthesis of 6-((3-(1,1,1,5,5,5-hexamethyl-3-((trimethylsilyl)oxy)trisiloxan-3-yl)propyl)amino)-N,N,N-trimethyl-6-oxohexan-1-aminium iodide (Surfactant 3)

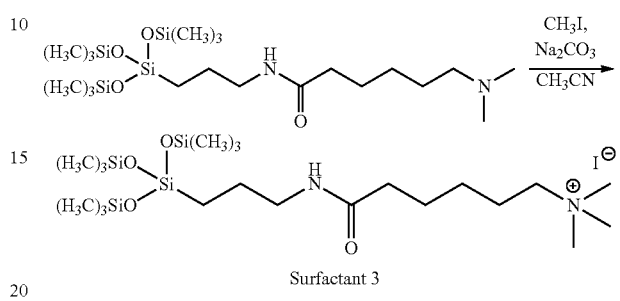

Surfactant 3

Surfactant 1 (1.00 g, 2.02 mmol, 1 equiv.) was dissolved in acetonitrile (10 mL) in a 100 mL round bottom flask. Next, Na$_2$CO$_3$ (0.26 g, 2.42 mmol, 1.2 equiv.) was added and the mixture was stirred for 10 minutes. Methyl iodide (0.377 mL, 6.06 mmol, 3 equiv.) was added and the reaction was heated at 40° C. for 24 hours. The cooled reaction mixture was filtered, and the solvent was removed under vacuum to give Surfactant 3 as a slightly yellow solid in quantitative yield. —H NMR (500 MHz, DMSO) δ 0.09 (s, 27H), 0.38-0.42 (m, 2H), 1.23-1.26 (m, 2H), 1.37-1.40 (m, 2H), 1.52-1.55 (m, 2H), 1.65-1.69 (m, 2H), 2.08 (t, J=7.4 Hz, 2H), 2.99 (dd, J=13, 6.9 Hz, 2H), 3.04 (s, 9H), 3.24-3.33 (m, 2H).

The pure product is soluble in water and has surfactant properties. The halogen anions may be directly obtained from the N-alkylation reaction, and other desired counter anions may be obtained by anion exchange.

Example 2b

Determination of Physical Properties of Surfactant 3

Figure 2:
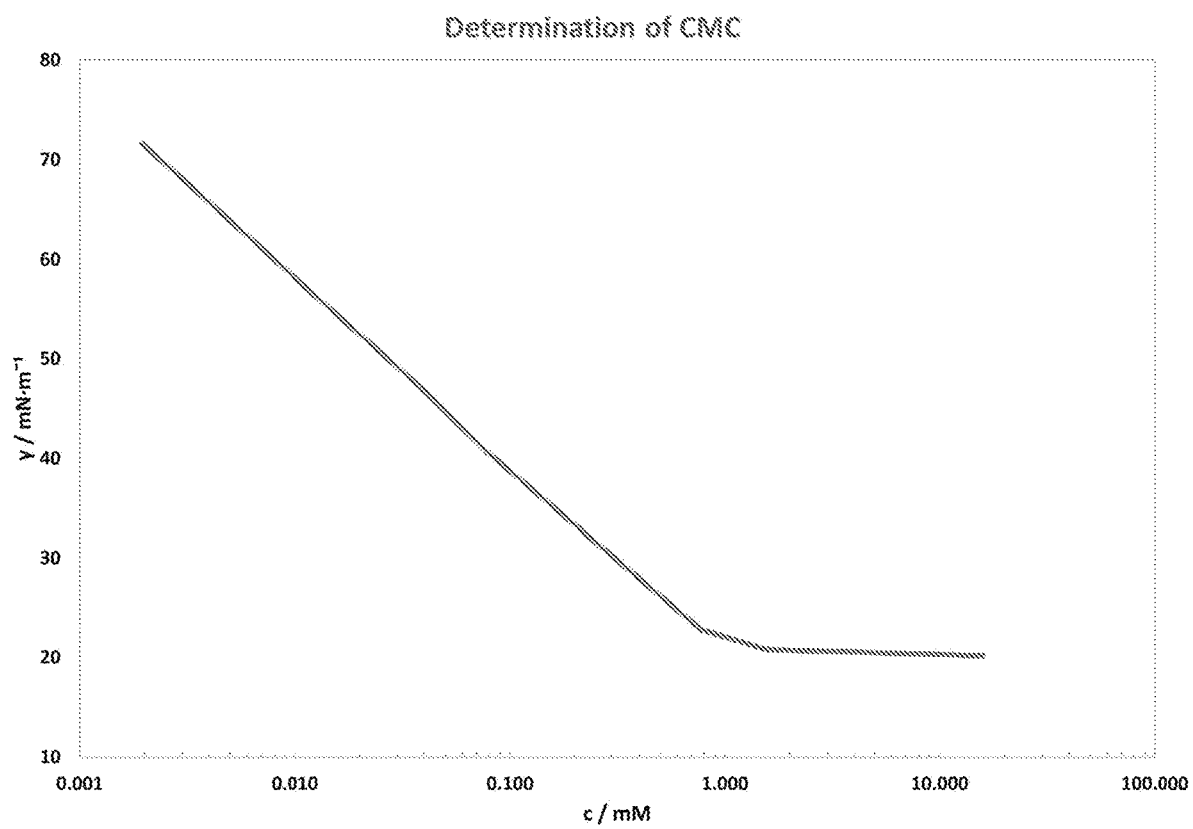
FIG. 2 shows a plot of surface tension versus concentration for Surfactant 3 as described in Example 2b.

The critical micelle concentration (CMC) for Surfactant 3 was measured. From the surface tension change with concentration in water, the CMC was determined to be about 1.6 mmol. The plateau value of minimum surface tension that can be reached by this surfactant is around 20 mN/m, indicating that the surfactant has outstanding interfacial activity. These results are plotted as surface tension versus concentration in FIG. 2.

Figure 3:
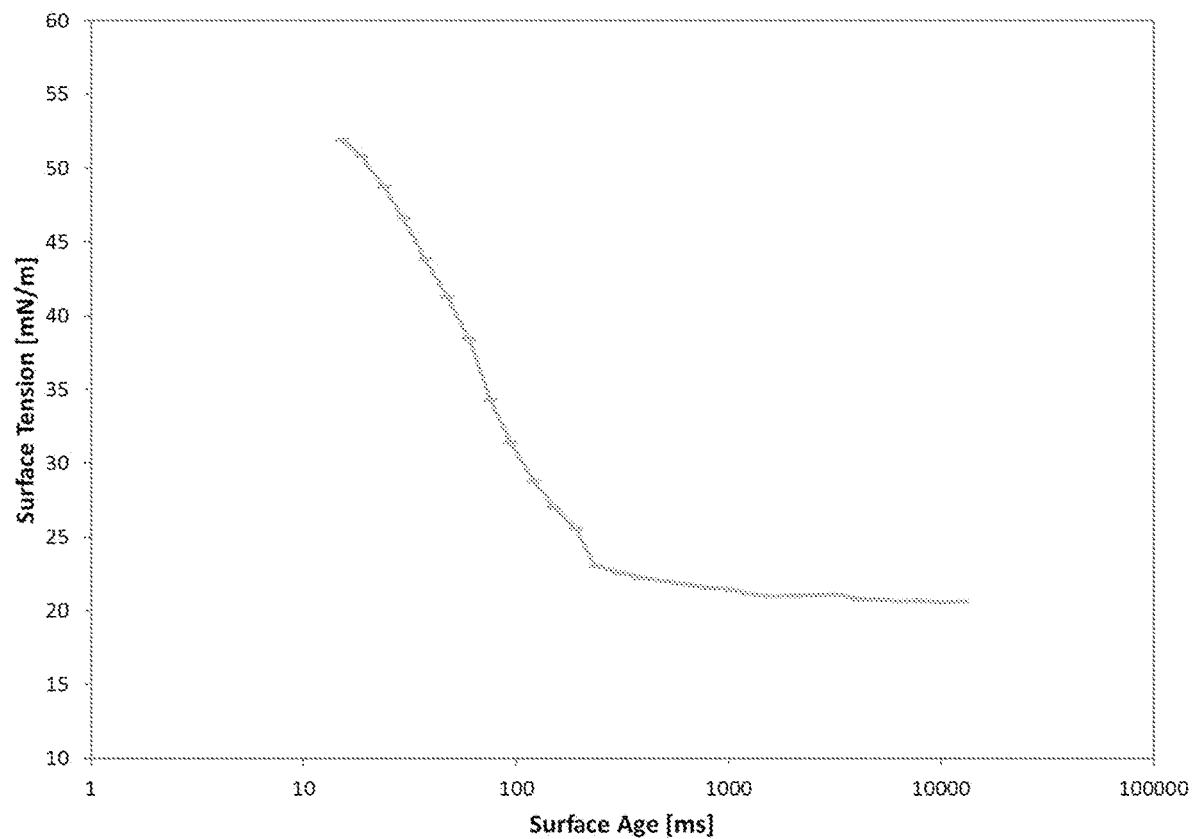
FIG. 3 shows a plot of dynamic surface tension as change in surface tension versus time for Surfactant 3 as described in Example 2b.

The dynamic surface tension of Surfactant 3 was determined with a bubble pressure tensiometer which measures the change of surface tension of a freshly created air-water interface with time. FIG. 3 shows a plot of the results as surface tension versus time and demonstrates that Surfactant 3 fully saturated the interface in less than 500 ms, making it exceptionally fast in terms of interfacial adsorption.

In addition to Surfactant 3's ability to lower both interfacial and surface tension, formulations containing only Surfactant have exceptional wetting properties. For example, hydrophobic substrates such as polyethylene and polypropylene exhibit a total surface wetting with a contact angle of 0°. On oleophobic and hydrophobic substrates such as Teflon, the measured contact angle was extremely low, 10.5° (Table 2).

(The opening text above example 1a: "contact angle goniometer (OCA 15 Pro, DataPhysics GmbH) equipped with a digital camera.")

TABLE 2

| Substrate | CA of Surfactant 3 (°) | Concentration | CA of water (°) |
|---|---|---|---|
| Teflon | 10.5 | 10× CMC | 119 |
| Polyethylene | 0 | 10× CMC | 91.5 |
| Polypropylene | 0 | 10× CMC | 93.3 |
| Nylon | 0 | 10× CMC | 50 |
| Polyethylene terephthalate | 0 | 10× CMC | 65.3 |

Example 3a

Synthesis of 6-((3-(1,1,1,5,5,5-hexamethyl-3-((trimethylsilyl)oxy)trisiloxan-3-yl)propyl)amino)-N,N-dimethyl-6-oxohexan-1-amine oxide (Surfactant 4)

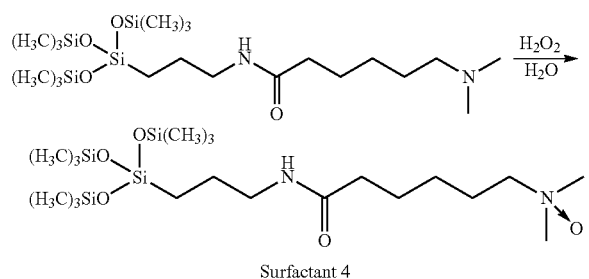

Surfactant 4

Surfactant 1 (1.00 g, 2.02 mmol, 1 equiv.) was added to distilled water (80 mL) in a 100 mL round bottom flask, followed by 50% hydrogen peroxide (1.15 mL, 20.2 mmol, 10 equiv.). The reaction was refluxed for 12 hours, then concentrated under vacuum. The residue was washed three times with acetone to give Surfactant 4 in 99% yield. 1H NMR (500 MHz, DMSO) δ 0.09 (s, 27H), 0.38-0.44 (m, 2H), 1.21-1.25 (m, 2H), 1.35-1.42 (m, 2H), 1.50-1.55 (m, 2H), 1.71-1.75 (m, 2H), 2.05-2.08 (m, 2H), 2.97-3.00 (m, 2H), 3.01 (s, 9H), 3.11-3.14 (m, 2H).

Example 3b

Determination of Physical Properties of Surfactant 4

Figure 4:
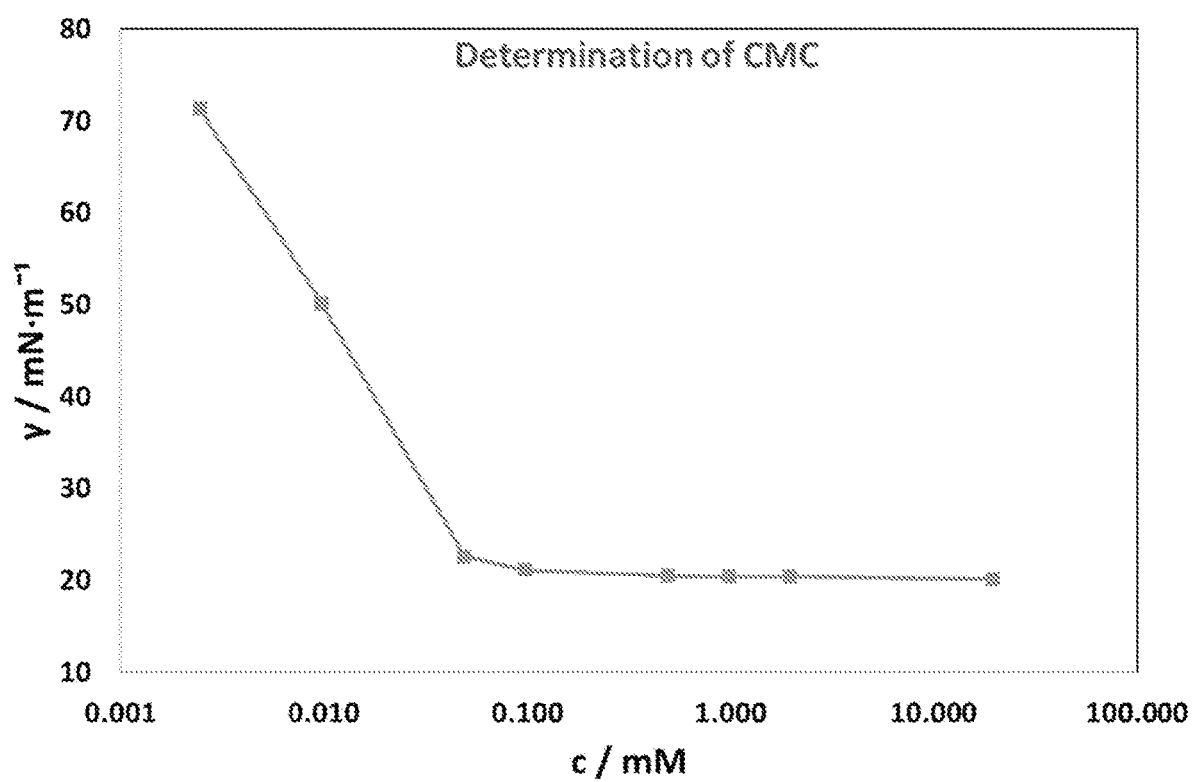
FIG. 4 shows a plot of surface tension versus concentration for Surfactant 4 as described in Example 3b.

The critical micelle concentration (CMC) for Surfactant 4 was measured. From the surface tension change with concentration in water, the CMC was determined to be about 0.49 mmol. The plateau value of minimum surface tension that can be reached by this surfactant is about 20 mN/m, indicating that the surfactant has outstanding interfacial activity. These results are plotted as surface tension versus concentration in FIG. 4.

Figure 5:
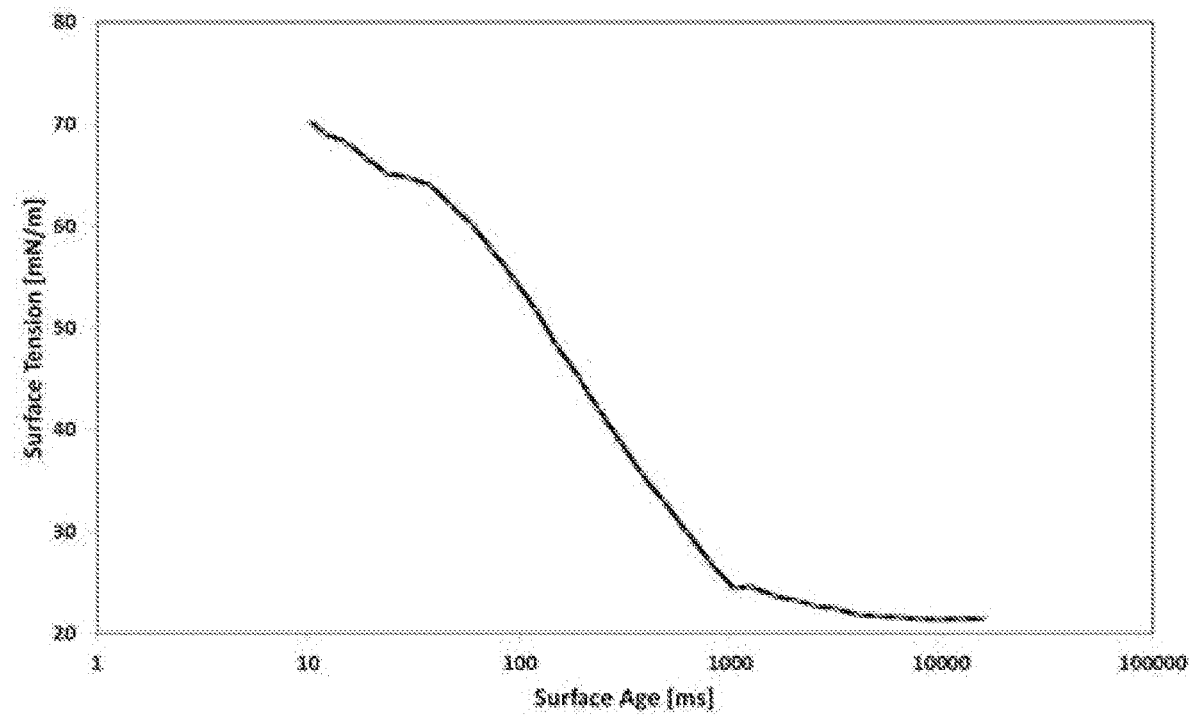
FIG. 5 shows a plot of dynamic surface tension as change in surface tension versus time for Surfactant 4 as described in Example 3b.

The dynamic surface tension of Surfactant 4 was determined with a bubble pressure tensiometer. FIG. 5 shows a plot of the results as surface tension versus time and demonstrates that Surfactant 4 fully saturated a freshly created air-water interface in one second or less, making it fast in terms of interfacial adsorption.

In addition to Surfactant 4's ability to lower both the interfacial and surface tension, formulations containing only Surfactant 4 in concentrations of 1-100×CMC have exceptional wetting properties. For example, a solution of Surfactant 4 in water at a concentration of 10×CMC exhibits a 0° contact angle on hydrophobic substrates such as polyethylene and polypropylene, and 10.6° on oleophobic and hydrophobic substrates such as Teflon. These contact angles are extremely low in comparison with the contact angle of water on the same substrate (Table 3).

TABLE 3

| Substrate | CA of Surfactant 4 (°) | Concentration | CA of water (°) |
|---|---|---|---|
| Teflon | 10.6 | 10× CMC | 119 |
| Polyethylene | 0 | 10× CMC | 91.5 |
| Polypropylene | 0 | 10× CMC | 93.3 |
| Nylon | 0 | 10× CMC | 50 |
| Polyethylene terephthalate | 0 | 10× CMC | 65.3 |

Example 4a

Synthesis of 4-((6-((3-(1,1,1,5,5,5-hexamethyl-3-((trimethylsilyl)oxy)trisiloxan-3-yl)propyl)amino)-6-oxohexyl)dimethylammonio)butane-1-sulfonate (Surfactant 5)

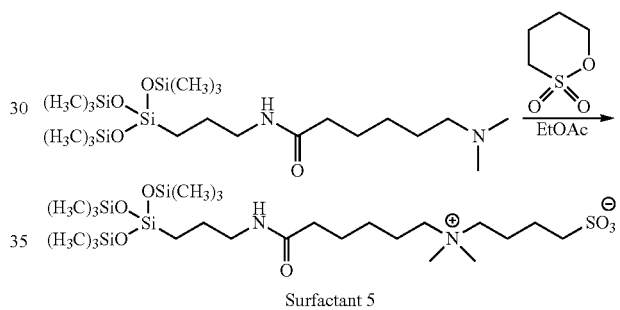

Surfactant 5

Surfactant 1 (1.00 g, 2.02 mmol, 1 equiv.) was added to ethyl acetate (EtOAc) (30 mL) in a 100 mL round bottom flask, followed by 1,2-butane sultone (0.27 mL, 2.2 mmol, 1.1 equiv.). The reaction was refluxed for 12 hours, after which the solvent was removed and the resultant white waxy solid was washed with acetone to give Surfactant 5 in 50% yield. 1H NMR (500 MHz, DMSO) δ 0.10 (s, 27H), 0.38-0.46 (m, 2H), 1.23-1.27 (m, 2H), 1.37-1.68 (m, 10H), 1.73-1.78 (m, 2H), 2.45-2.48 (m, 2H), 2.97-3.01 (m, 8H), 3.18-3.21 (m, 2H), 3.23-3.27 (m, 2H).

Example 4b

Determination of Physical Properties of Surfactant 5

Figure 6:
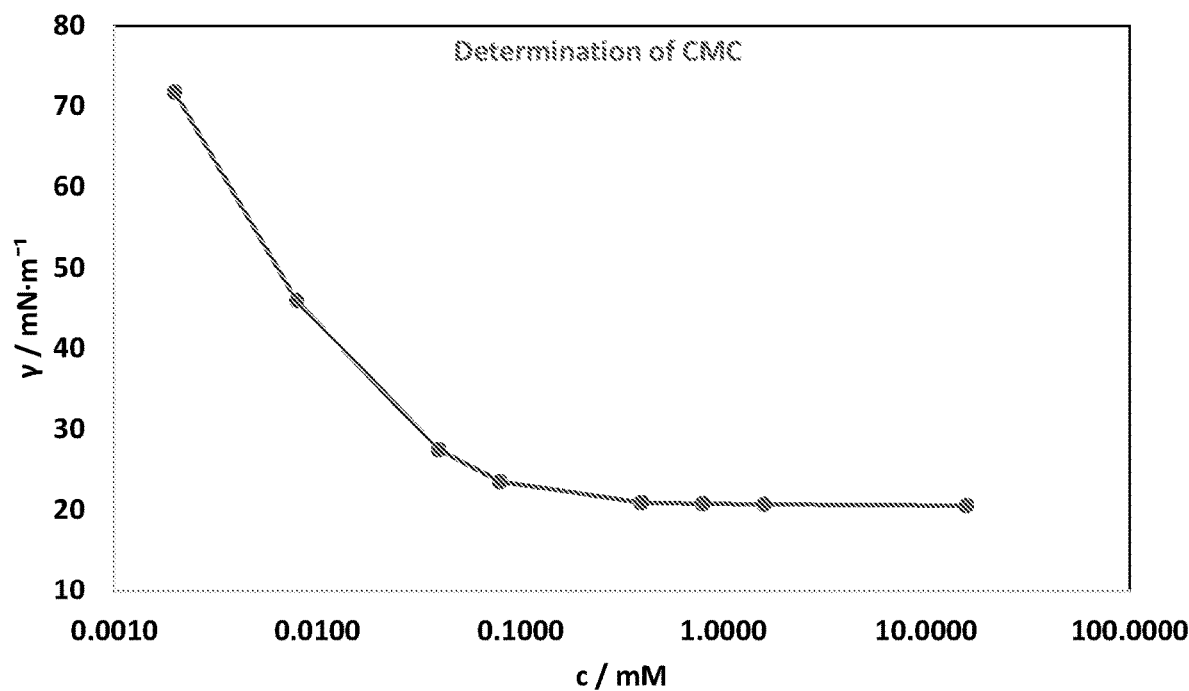
FIG. 6 shows a plot of surface tension versus concentration for Surfactant 5 as described in Example 4b.

The critical micelle concentration (CMC) for Surfactant 5 was measured. From the surface tension change with concentration in water, the CMC was determined to be about 0.39 mmol. The plateau value of minimum surface tension that can be reached by this surfactant is about 21 mN/m, indicating that the surfactant has outstanding interfacial activity. These results are plotted as surface tension versus concentration in FIG. 6.

Figure 7:
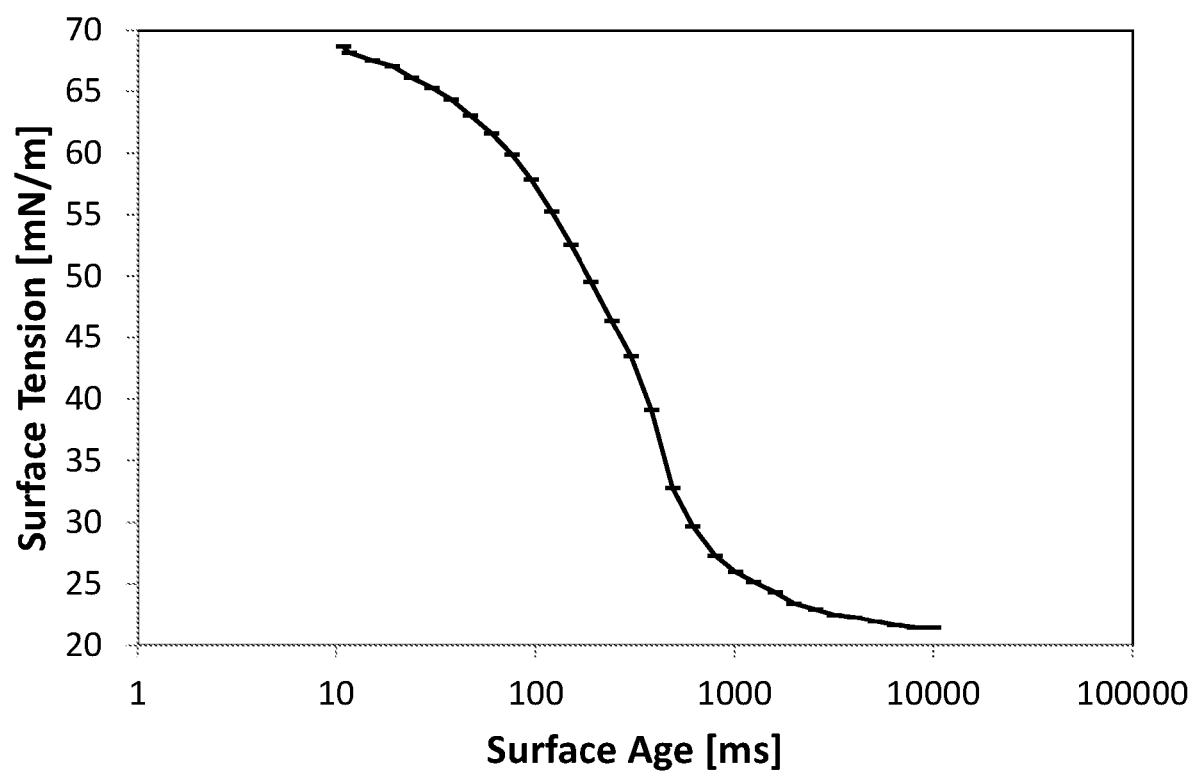
FIG. 7 shows a plot of dynamic surface tension as change in surface tension versus time for Surfactant 5 as described in Example 4b.

The dynamic surface tension of Surfactant 5 was determined with a bubble pressure tensiometer. FIG. 7 shows a plot of the results as surface tension versus time and demonstrates that Surfactant 5 fully saturated a freshly created air-water interface in one second or less, making it fast in terms of interfacial adsorption.

Finally, a solution of Surfactant 5 in water at a concentration of 10×CMC exhibits a 0° contact angle on hydrophobic substrates such as polyethylene and polypropylene, and 10.2° on oleophobic and hydrophobic substrates such as Teflon. These contact angles are extremely low in comparison with the contact angle of water on the same substrate (Table 4).

TABLE 4

| Substrate | CA of Surfactant 5 (°) | Concentration | CA of water (°) |
|---|---|---|---|
| Teflon | 10.2 | 10× CMC | 119 |
| Polyethylene | 0 | 10× CMC | 91.5 |
| Polypropylene | 0 | 10× CMC | 93.3 |
| Polyethylenterephthalate | 0 | 10× CMC | 65.3 |
| Nylon | 0 | 10× CMC | 50 |
| Polyethylene-HD | 0 | 10× CMC | 93.6 |

Example 5

Formulation for a Solid Oral Dosage

In this Example, a formulation for use in a solid oral dosage is described. This formulation is useful in in providing a solid oral dosage that includes at least one Active such as a drug and is readily manufactured, stored, and administered to, or by, a human or an animal patient. The components of the formulation are shown below in Table 5. Additionally, the formulation may include other compounds such as sweeteners, flavoring compounds.

The following process is used to make drug-containing particles of the Active oxcarbazepine. The following ingredients in the amounts indicated are used.

TABLE 5

| INGREDIENT | AMT (% WT.) | AMT (% WT.) | AMT (% WT.) | AMT (% WT.) | AMT (% WT.) | AMT (% WT.) |
|---|---|---|---|---|---|---|
|  | 1 | 2 | 3 | 4 | 5 | 6 |
| Oxcarbazpine | 67.5 | 67.8 | 65-70 | 65-70 | 66.7 | 65.2 |
| Microcrystalline cellulose | 22.5 | 22.6 | 21-24 | 21.7-23.3 | 22.2 | 21.7 |
| Hydroxypropylcellulose | 3.8 | 3.8 | 2.5-5 | 2.6-5 | 2.6 | 4.8 |
| Inventive Surfactant | 2.8 | 1.4 | 1-5 | 1.4-4.2 | 4.1 | 4 |
| Crosscarmel lose sodium | 3.4 | 4.4 | 2.4-5 | 2.4-4.5 | 4.3 | 4.2 |
|  | 7 | 5 | 9 | 10 | 11 | 12 |
| Oxcarbazpine | 70 | 68.6 | 66.4 | 68 | 67 | 68.3 |
| Microcrystalline cellulose | 23.3 | 22.9 | 22.2 | 22.7 | 22.3 | 22.8 |
| Hydroxypropylcellulose | 2.7 | 2.7 | 4.9 | 2.6 | 4.9 | 5 |
| Inventive Surfactant | 1.5 | 1.4 | 4.1 | 4.2 | 1.4 | 1.4 |
| Crosscarmel lose sodium | 2.5 | 4.5 | 2.4 | 2.4 | 1.4 | 2.4 |

TABLE 6

| Material | % (w/w) | Amount per batch (g) |
|---|---|---|
| Oxcarbazepine | 67.5% | 2295.0 |
| Microcrystalline cellulose (Avicel PH101, FMC) | 22.5% | 765.0 |
| Croscarmellose sodium (Ac-Di-Sol SD-711, FMC) | 3.4% | 115.6 |

TABLE 6-continued

| Material | % (w/w) | Amount per batch (g) |
|---|---|---|
| Inventive Surfactant | 2.8% | 95.2 |
| Hydroxypropyl cellulose (HPC-SL | 3.8% | 129.2 |

The exemplary drug-containing particles are made by wet granulation at a scale of 4 L to 200 L. The following equipment and operating parameters were used.

TABLE 7

| Equipment | Manufacturer | Location | Parameters |
|---|---|---|---|
| High Shear Granulator (GRAL 25) | Collette | Wommelgem, Belgium | Bowl size = 25 L Mixer and chopper on low speed Binder (water) flow rate 95 mL/min |
| Fluid Bed Processor (FLM.3) | Vector | Marion, IA | 50 C. inlet temperature ~40 cfm air flow Dry to LOD 1-2% |
| Comil (197S) | Quadro | Waterloo, Ontario, Canada | 3000 rpm Multiple passes (050G, 016C, 018R) |

All powders were weighed and added to the bowl of the high shear granulator. The dry powder was mixed at low speed for 1 minute. With the mixer and chopper on low speed, water was added at a rate of 95 mL/min for a total of 1164 g water (25.5% of final wet weight). The granulator was stopped once during the process to scrape the bowl. The wet granulation was dried in a fluid bed drier at 50° C. to an LOD of 1-2%. Using a Comil at 3000 rpm, the dried material was milled through a series of screens to reduce the particle size to an acceptable range for 3DP. The milling began through a 050G screen and ended through a 018R screen. For most batches, a pass was made through an intermediate Screen (016C) to prevent blinding.

Example 6

Preparation of a Three-Dimensionally Printed Orodispersible Dosage Form

The following process is used to prepare a taste-masked three-dimensionally printed orodispersible dosage form comprising a matrix comprising bound drug-containing particles of oxcarbazepine. The components of the printing fluid are shown below in Table 8.

TABLE 8

| Printing Fluid | I-A |
|---|---|
| Water (wt. %) | 85 |
| Glycerin wt. %) | 5 |
| Ethanol (wt. %) | 5 |
| Surfactant (wt. %) | 1 |
| Sucralose (wt. %) | 2 |

The components of the bulk powders for runs II-A to II-H are shown below in Table 9, with amounts indicated by weight percentage (% wt.).

TABLE 9

| Bulk powder | II-A | II-B | II-C | II-D | II-E | II-F | II-G | II-H |
|---|---|---|---|---|---|---|---|---|
| OXC-containing particles | 55 | 60 | 65 | 75 | 80 | 70 | 70 | 60 |
| Avicel PH101 | 4.5 | 4.5 | 4.5 | 4.5 | 4.5 | 19.5 | 9.5 | 9.5 |
| Mannitol | 33 | 28 | 23 | 13 | 8 | 0 | 10 | 20 |
| Polyvinylpyrrolidone | 7 | 7 | 7 | 7 | 7 | 10 | 10 | 10 |
| Silica | 0.5 | 0.5 | 0.5 | 0.5 | 0.5 | 0.5 | 0.5 | 0.5 |
| HPC SL (hydroxypropylcellulose) | | | | | | | | |

The components of the bulk powders for runs II-L to II-S and H-T are shown below in Table 10, with amounts indicated by weight percentage (% wt.)

TABLE 10

| Bulk powder | II-L | II-M | II-N | II-O | II-P | II-Q | II-R | II-S | II-T |
|---|---|---|---|---|---|---|---|---|---|
| OXC-containing particles | 70 | 70 | 70 | 60 | 60 | 63.5 | 63.5 | 63.5 | 63.5 |
| Avicel PH101 | 9.5 | 0 | 0 | 4.5 | 4.5 | 0 | 0 | 0 | 0 |
| Mannitol | 13 | 19.5 | 22.5 | 28 | 28 | 36 | 15 | 24.9 | 9 |
| Polyvinylpyrrolidone | 7 | 10 | 7 | 7 | 0 | 0 | 0 | 0 | 0 |
| Silica | 0.5 | 0.5 | 0.5 | 0.5 | 0.5 | 0.5 | 0.5 | 0.5 | 0.5 |
| HPC SL (hydroxypropylcellulose) | 0 | 0 | 0 | 0 | 7 | — | — | — | — |
| RFC SLI (hydropropylcellulose) | — | — | — | — | — | 0 | 0 | 0 | 6 |

Any three-dimensional printer equipment assembly, known or mentioned herein, can be used. An incremental layer of bulk powder of predetermined thickness is spread onto a prior layer of powder, and printing fluid is applied to the incremental layer as droplets according to a predetermined Saturation level, line spacing and printing fluid flow-rate to bind the particles therein. This two-step process is completed until a matrix comprising the target amount of printed incremental layers. The following printing parameters are used on a Z-Corp lab scale printer (Model Z310). The printer is equipped with a HP-10 printhead and is operated at a scan rate of droplet size of 30-60 um and line spacing of 450-600 um. A solid print pattern is used throughout the dosage form. The specified combination of printing fluid formulation and bulk powder formulation is used. A layer thickness of 0.008 to 0.011 inches is used. A saturation of 90 to 116% is used. The printing fluid I-A is used. Many different combinations of the drug-containing particles Nos. 1-12 and bulk powder formulations IIA through II-T are used. The printed matrix is separated from loose unprinted pow der and the printed matrix is dried by any suitable means to reduce the amount of solvent and moisture to a desired level, thereby producing the final 3D orodispersible dosage form. The dispersion time, surface texture (Smoothness) and hardness of the dosage form are then determined.

Example 7

Preparation of a Taste-Masked Three-Dimensionally Printed Orodispersible Dosage Forms with Varying Architecture Among Incremental Layers The 3DP process described above is followed; however, it can be conducted in several different ways to prepare dosage forms of different architecture varying in hardness and composition of incremental layers. The following processes provide a dosage form having greater hardness in the upper and lower surfaces as compared to the hardness of the interior portion of the dosage form. This tactic helps create sections within a dosage form with different mechanical properties. This approach is used to design dosage forms in which the composition of the top and bottom layers is different from the middle layers. This design allows the dosage forms to have stronger top and bottom layers, thereby increasing hardness and reducing friability, and a large middle portion with lower hardness, which enables the dosage form to disperse rapidly.

Method A:

In this process, the amount of binder deposited in different incremental layers or within different predefined regions within the same incremental layers is varied. The process of Example 6 is followed to prepare these dosage forms, except that the amount of binder, by way of the printing fluid, deposited onto the powder is varied among the incremental powder layers by using printing fluids differing in concentration of binder.

Method B:

The process defined above is followed to prepare these dosage forms, except that the amount of printing fluid deposited onto the powder is varied among the incremental powder layers. The upper and lower incremental layers receive a higher amount of printing fluid and the incremental layers of the middle portion receive a lower amount of printing fluid.

Method C:

In this process, the printing pattern, employed for the upper and lower incremental layers of the dosage form, is a solid pattern. The printing pattern for the middle portion of incremental layers.

Method D:

In this process, the printing pattern, employed for the upper and lower incremental layers of the dosage form, is a solid pattern. The printing pattern for the middle portion of incremental layers is an annular/hollow high saturation printing with no printing in the area surrounded by an annulus.

Method E:

In this process, the printing pattern, employed for the upper and lower incremental layers of the dosage form, is a Solid pattern. The printing pattern for the middle portion of incremental layers is a combination of interior gray scale printing surrounded by an exterior high Saturation printing.

Example 8

Preparation of an Emulsion for Intravenous Injection

Preparing of the Active, Aprepitant Emulsions for Intravenous Injection To prepare the aprepitant emulsion, an oil phase was first prepared by combining 750 mg of the Active aprepitant and 15.0 g of egg lecithin (LIPOID E 80) with 12.0 ml of ethanol. This mixture was dissolved by heating and stirring at 60° C. and 200 rpm for 15 min. To the resultant solution was added into 10.0 g of soybean oil. Heating at 60° C. and stirring at 200 rpm was continued for another 15 min. The aqueous phase was prepared by dissolving 5.60 g of sucrose and 0.500 g of the inventive surfactant in 70.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-IIOL, F12Y interaction chamber) at a pressure of 18,000 psi. The resultant fine emulsion was sterilized by passing it through a 0.2 µm nylon syringe filter (Corning). The details of the emulsion composition are provided in Table 11 below. By dynamic light scattering (Malvern® Zetasizer Nano), the intensity-weighted particle size analyzed using non-negative least squares (NNLS) fit gave a Peak 1 diameter of 99 nm. The intensity-weighted mean particle size determined using cumulant fit provided a Z-average diameter of 87 nm. The zeta potential was measured to be −43 mV by laser Doppler micro-electrophoresis (Malvern® Zetasizer Nano zs). The pH of the injectable emulsion was 8.74. This aprepitant-containing emulsion can be injected as-is or diluted for infusion with 5% dextrose or 0.9% saline.

TABLE 11

| Component | Amount (g) | Concentration (w/w %) | Ratio to Aprepitant |
| --- | --- | --- | --- |
| Aprepitant | 0.750 | 0.679 | |
| Lipoid E 80 | 15.0 | 13.6 | 20 |
| Soybean Oil | 10.0 | 9.05 | 13.3 |
| Ethanol | 8.59 | 7.78 | 11.5 |
| Sucrose | 5.60 | 5.07 | 7.5 |
| Inventive Surfactant | 0.500 | 0.453 | 0.667 |
| Water for Injection | 70.0 | 63.4 | 93.3 |
| Total | 110 | 100 | |

[1] Final amount after taking into account the ethanol that was evaporated during processing.

Example 9

Preparation of Emulsion for Intravenous Injection

To prepare the Active aprepitant in an emulsion, an oil phase was first prepared by combining 450 mg of aprepitant and 9.00 g of egg lecithin (LIPOID E 80) with 4.0 ml of ethanol. This mixture was dissolved by heating and stirring at 60° C. and 200 rpm for 15 min. To the resultant solution was added 6.00 g of soybean oil. Heating at 60° C. and stirring at 200 rpm was continued for another 15 min. The aqueous phase was prepared by dissolving 3.36 g of sucrose and 0.300 g of surfactant in 42.0 ml of water for injection. This mixture was stirred at 300 rpm at room temperature for 30 min. The aqueous phase was then added to the oil phase and subsequently subjected to high-speed homogenization (Ultra-Turrax® IKA T25) at a speed of 20,000 rpm for 1 min to produce the crude emulsion. This crude emulsion was then passed 8 times through an ice-cooled high-pressure microfluidizer (Microfluidizer® M-IIOL, F12Y interaction chamber) at a pressure of 18,000 psi. The resultant fine emulsion was sterilized by passing it through a 0.2 µm nylon syringe filter (Corning). The details of the emulsion composition are provided in Table 12. Via analysis by dynamic light scattering (Malvern® Zetasizer Nano ZS), the intensity-weighted particle size analyzed using NNLS fit gave a Peak 1 diameter of 127 nm. The intensity-weighted mean particle sized determined using cumulant fit provided a Z-average diameter of 101 nm. The zeta potential was measured to be −4 7 mV by laser Doppler micro-electrophoresis (Malvern® Zetasizer Nano ZS. The pH of the injectable emulsion was 8.77. This aprepitant-containing emulsion can be injected as is or diluted with 5% dextrose or 0.9% saline.

TABLE 12

| Component | Amount (g) | Concentration (w/w %) | Ratio to Aprepitant |
| --- | --- | --- | --- |
| Aprepitant | 0.450 | 0.714 | |
| Lipoid E 80 | 9.00 | 14.3 | 20 |
| Soybean Oil | 6.00 | 9.52 | 13.3 |
| Ethanol | 1.89 | 3.00 | 4.20 |
| Sucrose | 3.36 | 5.33 | 7.47 |
| Inventive Surfactant | 0.300 | 0.476 | 0.667 |
| Water for Injection | 42.0 | 66.7 | 93.3 |
| Total | 63.0 | 10 | |

[1] Final amount after taking into account the ethanol that was evaporated during processing.

Aspects

Aspect 1 is a solid formulation for a healthcare product comprising at least one surfactant of Formula I,

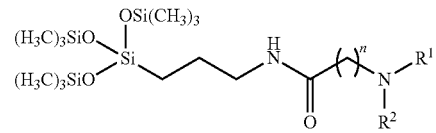

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; an Active ingredient; and an excipient.

Aspect 2 is a liquid formulation, comprising at least one surfactant of Formula I,

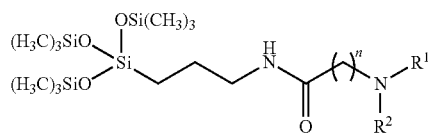

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one Active ingredient; and water.

Aspect 3 is an emulsion for healthcare, comprising at least one surfactant of Formula I,

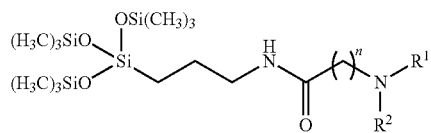

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate; n is an integer from 1 to 12; the terminal nitrogen is optionally further substituted with $R^3$, wherein $R^3$ is selected from the group consisting of hydrogen, oxygen, hydroxyl, and $C_1$-$C_6$ alkyl; an optional counterion associated with the compound which, if present, is selected from the group consisting of chloride, bromide, and iodide; at least one Active ingredient; and aqueous phase; and a non-aqueous phase.

Aspect 4 is the formulation of Aspects 1-3, further comprising a sweetening agent.

Aspect 5 is the formulation of Aspects 1-4, further comprising a flavoring agent.

Aspect 6 is the formulation of Aspects 1-5, further comprising a coloring agent.

The invention claimed is:
1. A solid healthcare formulation, comprising:
at least one surfactant of Formula I,

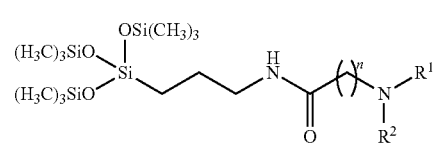

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;
n is an integer from 1 to 12;
the terminal nitrogen is optionally further substituted with $R^3$, wherein $R^3$ is selected from the group consisting of hydrogen, oxygen, hydroxyl, and $C_1$-$C_6$ alkyl;
an optional counterion associated with the compound which, if present, is selected from the group consisting of chloride, bromide, and iodide; and
at least one Active ingredient.
2. The formulation according to claim 1, wherein the at least one Active is selected from the group consisting of: a drug, a protein, a cell, a tissue, a vitamin, a supplement, and a mineral.
3. The formulations according to claim 1, further including at one or more excipients.
4. The formulations according to claim 3, wherein the one or more excipients are selected from the group consisting of: binders, fillers, disintegrants, salts, colorants, sweeteners, and flavorants.
5. The formulations according to claim 1, wherein the formulation is configured as a powder, a tablet, or a capsule.
6. A liquid formulation for healthcare, comprising:
at least one surfactant of Formula I,

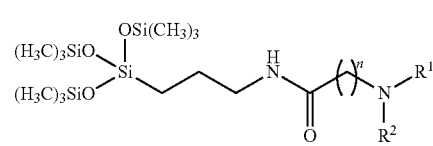

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;

n is an integer from 1 to 12;

the terminal nitrogen is optionally further substituted with $R^3$, wherein $R^3$ is selected from the group consisting of hydrogen, oxygen, hydroxyl, and $C_1$-$C_6$ alkyl;

an optional counterion associated with the compound which, if present, is selected from the group consisting of chloride, bromide, and iodide;

at least one Active ingredient; and an aqueous component.

7. The formulation according to claim 6, further including a buffer.

8. The formulation according to claim 6, further including one or more of the following: a sweetener, a flavorant, a colorant, and/or a preservative.

9. The formulation according to claim 6, further including a thickener.

10. The formulation according to claim 9, wherein the formulation is one of the following: a drop, a paste, a salve, a lotion, or an ointment.

11. An emulsion for healthcare, comprising:

at least one surfactant of Formula I,

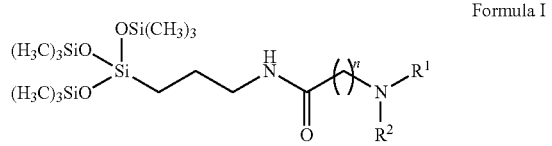

Formula I wherein $R^1$ and $R^2$ may be the same or different, and comprise at least one group selected from the group consisting of $C_1$-$C_6$ alkyl, optionally the $C_1$-$C_6$ alkyl may include one or more of oxygen, nitrogen, or sulfur atoms or groups that include at least one of these atoms, and the alkyl chain may be optionally substituted with one or more substituents selected from the group consisting of hydroxyl, amino, amido, sulfonyl, sulfonate, carbonyl, carboxyl, and carboxylate;

n is an integer from 1 to 12;

the terminal nitrogen is optionally further substituted with $R^3$, wherein $R^3$ is selected from the group consisting of hydrogen, oxygen, hydroxyl, and $C_1$-$C_6$ alkyl;

an optional counterion associated with the compound which, if present, is selected from the group consisting of chloride, bromide, and iodide; and at least one Active ingredient;

an aqueous phase; and a non-aqueous phase.

12. The emulsion of claim 11, further including a buffer.

13. The emulsion of claim 11, further including one or more of the following: a sweetener, a flavorant, a colorant, and/or a preservative.

* * * * *